United States Patent
Ammour et al.

(10) Patent No.: US 10,640,773 B2
(45) Date of Patent: May 5, 2020

(54) PLANT SRNA EXTRACT OR PLANT MIRNA FOR USE AS AN IMMUNOSUPPRESSIVE AGENT

(71) Applicant: Fondazione Edmund Mach, S. Michele all'Adige (IT)

(72) Inventors: Azeddine Si Ammour, Trento (IT); Roberto Viola, Località San Donaà (IT); Duccio Cavalieri, Trento (IT); Lisa Rizzetto, Trento (IT)

(73) Assignee: Fondazione Edmund Mach, S. Michele all'Adige (IT)

( * ) Notice: Subject to any disclaimer, the term of this patent is extended or adjusted under 35 U.S.C. 154(b) by 0 days.

(21) Appl. No.: 15/307,119

(22) PCT Filed: Apr. 30, 2014

(86) PCT No.: PCT/EP2014/058888
§ 371 (c)(1),
(2) Date: Oct. 27, 2016

(87) PCT Pub. No.: WO2015/165535
PCT Pub. Date: Nov. 5, 2015

(65) Prior Publication Data
US 2017/0044542 A1    Feb. 16, 2017

(51) Int. Cl.
*A61K 48/00* (2006.01)
*C07H 21/02* (2006.01)
*C07H 21/04* (2006.01)
*C12N 15/117* (2010.01)
*C12N 15/113* (2010.01)
*A61K 31/7105* (2006.01)
*A23L 33/105* (2016.01)
*A23L 33/115* (2016.01)
*A61K 9/00* (2006.01)
*A61K 45/06* (2006.01)
*A61K 31/713* (2006.01)

(52) U.S. Cl.
CPC .......... *C12N 15/117* (2013.01); *A23L 33/105* (2016.08); *A23L 33/115* (2016.08); *A61K 9/0056* (2013.01); *A61K 31/713* (2013.01); *A61K 31/7105* (2013.01); *A61K 45/06* (2013.01); *C12N 15/113* (2013.01); *C12N 15/1136* (2013.01); *A23V 2002/00* (2013.01); *C12N 2310/141* (2013.01); *C12N 2310/17* (2013.01); *C12N 2320/31* (2013.01)

(58) Field of Classification Search
CPC ... A61K 31/713; C12N 2310/11; C07H 21/04
See application file for complete search history.

(56) References Cited

U.S. PATENT DOCUMENTS

| | | | |
|---|---|---|---|
| 5,534,499 A | 7/1996 | Ansell | |
| 5,820,873 A | 10/1998 | Choi et al. | |
| 5,885,613 A | 3/1999 | Holland et al. | |
| 6,320,017 B1 | 11/2001 | Ansell | |
| 8,481,508 B2 | 7/2013 | Ambati | |
| 2009/0155909 A1 | 6/2009 | McGonigle | |
| 2009/0155910 A1 | 6/2009 | McGonigle | |
| 2017/0044542 A1 | 2/2017 | Ammour et al. | |
| 2017/0044547 A1 | 2/2017 | Ammour et al. | |

FOREIGN PATENT DOCUMENTS

| | | |
|---|---|---|
| WO | 2009079532 A2 | 6/2009 |
| WO | 2009079548 A2 | 6/2009 |
| WO | WO-2009100502 A1 | 8/2009 |
| WO | WO-2012154824 A1 | 11/2012 |
| WO | 2014181344 A2 | 11/2014 |
| WO | 2015165535 A1 | 11/2015 |
| WO | 2015166060 A1 | 11/2015 |
| WO | 2015026249 A2 | 6/2017 |

OTHER PUBLICATIONS

Numnark et al. (BMC Genomics, 2012, 13(Suppl 7):S16).*
Ferretti et al. (Multiple Sclerosis, 2005, 11, 677-682).*
Li et al. (Plant Cell Rep, 2009, 28: 891-902).*
Frisullo et al. (Clinical Immunology, 2007, 124, 284-293).*
Wang et al. (International Journal of Molecular Sciences, 2018, 19, 2007, pp. 1-12).*
Alexopolou et al., Recognition of double-stranded RNA and activation of NF-kappaB by Toll-like receptor 3. Nature. 2001;413(6857):732-738.
Alvarez et al., Endogenous and synthetic microRNAs stimulate simultaneous, efficient, and localized regulation of multiple targets in diverse species. Plant Cell. 2006;18(5):1134-51.
Arteaga-Vazquez M. et al., A Family of MicroRNAs Present in Plants and Animals. The Plant Cell Online. Dec. 22, 2006;18(12):3355-69.
Axtell et al., Vive la difference: biogenesis and evolution of microRNAs in plants and animals. Genome Biology. 2011;12:221-234.
Baulcombe, D. RNA silencing. Trends Biochem. Sci. 2005;30:290-3.
Bernstein et al., Role for a bidentate ribonuclease in the initiation step of RNA interference. Nature. 2011;409:363-6.
Bi et al., MicroRNAs: novel regulators during the immune response. J Cell Physiol. Mar. 2009;218(3):467-72.
Bourquin et al., Immunostimulatory RNA oligonucleotides induce an effective antitumoral NK cell response through the TLR7. J Immunol. Nov. 15, 2009;183(10):6078-86.
Bridge et al., Induction of an interferon response by RNAi vectors in mammalian cells. Nat Genet 2003; 34(3):263-4.

(Continued)

*Primary Examiner* — Amy H Bowman

(74) *Attorney, Agent, or Firm* — Mintz Levin Cohn Ferris Glovsky and Popeo, P.C.; Ingrid A. Beattie

(57) ABSTRACT

The present invention relates to a plant sRNA extract for use as an immunosuppressive agent and to plant miRNA for use as an immunosuppressive agent.

10 Claims, 10 Drawing Sheets

Figure 1:
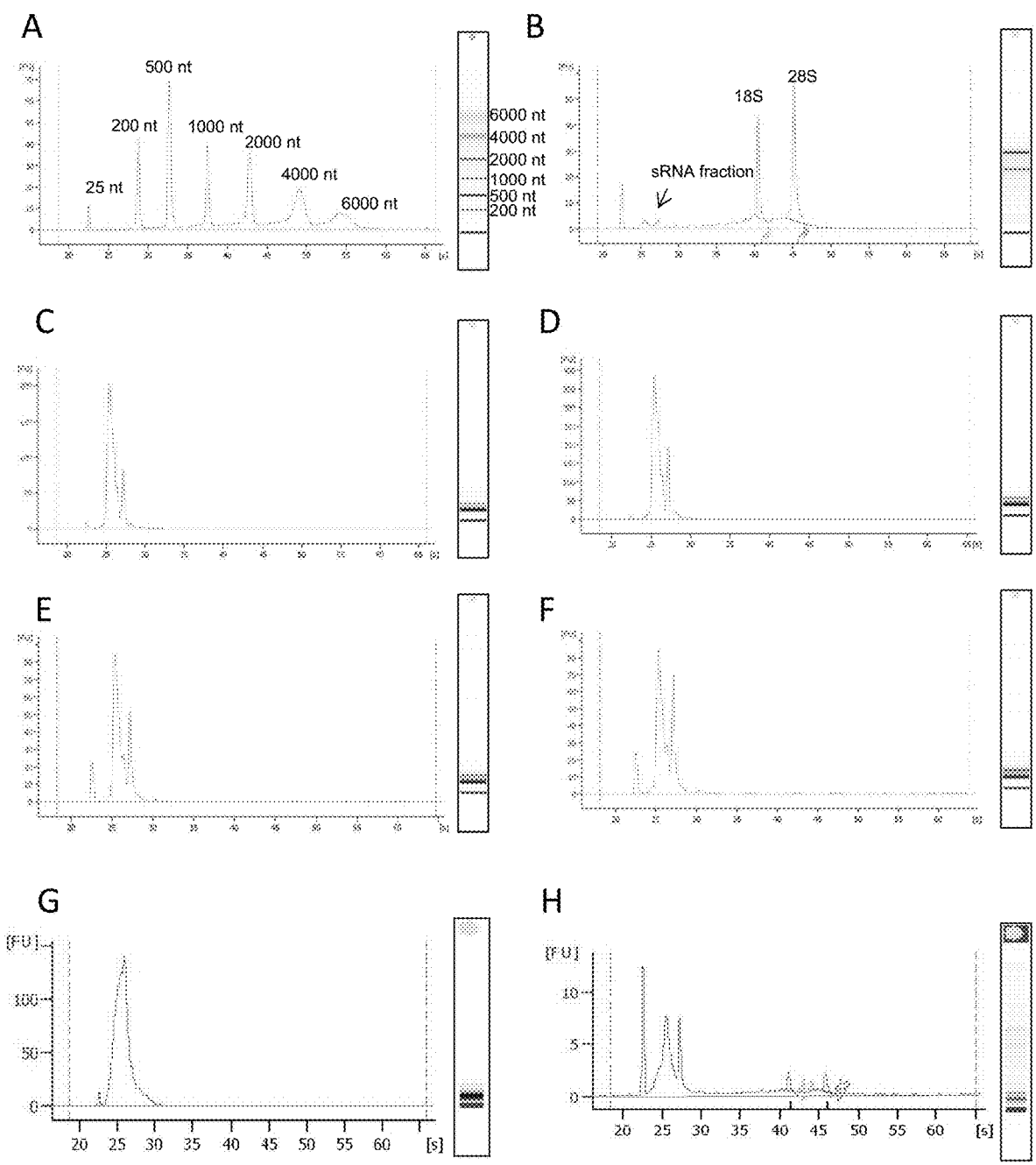

Specification includes a Sequence Listing.

(56) References Cited

OTHER PUBLICATIONS

Buck et al., Exosomes secreted by nematode parasites transfer small RNA to mammalian cells and modulate innate immunity. Nat Comm. 2014;5:5488.
Calin et al., MicroRNA signatures in human cancers. Nat Rev Cancer. Nov. 2006;6(11):857-66.
Carvalho et al., TLR3 essentially promotes protective class I-restricted memory CD8+T-cell responses to Aspergillus fumigatus in hematopoietic transplanted patients. Blood. Jan. 26, 2012;119(4):967-77.
Clayton et al., Adhesion and signaling by B cell-derived exosomes: the role of integrins. FASEB J 2004;18:977-9.
Contreras et al., MicroRNAs in inflammation and immune responses. Leukemia. Dec. 20, 2011;26(3):404-13.
Dunoyer et al., DICER-LIKE 4 is required for RNA interference and produces the 21-nucleotide small interfering RNA component of the plant cell-to-cell silencing signal. Nat Genet 2005;37:1356-60.
Elbashir et al., Duplexes of 21-nucleotides RNAs mediate RNA interference in cultured mammalian cells. Nature. 2001;411:494-8.
Fabbri et al., MicroRNAs bind to Toll-like receptors to induce prometastatic inflammatory response. PNAS. 2012;109(31):E2110-E2116.
Ge et al., Deep sequencing discovery of novel and conserved microRNAs in strawberry (*Fragaria*×*ananassa*). Physiol Plant. Jul. 2013;148(3):387-96.
Gomes et al., Non-Coding RNAs: Multi-Tasking Molecules in the Cell. Int. J. Mol. Sci. 2013;14:16010-39.
Haussecker et al., Human tRNA-derived small RNAs in the global regulation of RNA silencing. RNA. 2010;16(4):673-95.
Hornung et al., RNA recognition via TLR7 and TLR8. Handb Exp Pharmacol. 2008;183:71-86.
Johnnidis et al., Regulation of progenitor cell proliferation and granulocyte function by microRNA-223. Nature. 2008;451:1125-9.
Judge et al., Sequence-dependent stimulation of the mammalian innate immune response by synthetic siRNA. Nat Biotechnol. 2005;23(4):457-62.
Kapranov et al. RNA maps reveal new RNA classes and a possible function for pervasive transcription. Science. 2007;316(5830):1484-8.
Kariko et al., Small interfering RNAs mediate sequence-independent gene suppression and induce immune activation by signaling through toll-like receptor 3. J Imm. 2004;172:6545-9.
Kawai et al., Immune recognition of viral infection. Nature Immunology. 2006;7:131-7.
Kozomara et al., miRBase: integrating microRNA annotation and deep-sequencing data. Nucleic Acids Research. 2011;39:D152-D157.
Li et al., miR-181a is an intrinsic modulator of T cell sensitivity and selection. Cell. 2007;129:147-61.
Liu et al., MicroRNA-148/152 impair innate response and antigen presentation of TLR-triggered dendritic cells by targeting CaMKIIα. J Immunol. Dec. 15, 2010;185(12):7244-51.
Mallory et al., Functions of microRNAs and related small RNAs in plants. Nat, Genet. 2006;38:S31-36.
Meins et al., RNA silencing systems and their relevance to plant development. Annu. Rev. Cell Dev. Biol. 2005;21:297-318.
Meister et al., Mechanisms of gene silencing by double-stranded RNA. Nature. 2004;431:343-9.
Mix et al., Animal models of multiple sclerosis—potentials and limitations. Prog. Neurobiol. 2010;92: 386-404.
Montecalvo et al., Mechanism of transfer of functional microRNAs between mouse dendritic cells via exosomes. Blood. 2012;119:756-66.
Morelli et al., Endocytosis, intracellular sorting, and processing of exosomes by dendritic cells. Blood 2004;104:3257-66.
Niu et al., Expression of artificial microRNAs in transgenic *Arabidopsis thaliana* confers virus resistance. Nature Biotechnology. 2006;24:1420-8.
Nolte-'t Hoen et al., Deep sequencing of RNA from immune cell-derived vesicles uncovers the selective incorporation of small non-coding RNA biotypes with potential regulatory functions. Nucleic Acids Res. 2012;40(18):9272-85.
O'Connell et al., MicroRNA-155 promotes autoimmune inflammation by enhancing inflammatory T cell development. Immunity. Oct. 29, 2010;33(4):607-19.
O'Connell et al., Physiological and pathological roles for microRNAs in the immune system. Nat Rev Immunol. Feb. 2010;10(2):111-22.
Okahira et al., Interferon-beta induction through toll-like receptor 3 depends on double stranded RNA structure. DNA and Cell Biol. 2005;24(10):614-23.
Parizotto et al., In vivo investigation of the transcription, processing, endonucleolytic activity, and functional relevance of the spatial distribution of a plant miRNA. Genes Dev. 2007;18:2237-42.
Persson et al., The non-coding RNA oft he multidrug resistance-linked vault particle encodes multiple regulatory small RNAs. Nat Cell Biol. 2009;11(10):1268-71.
Pinto et al., Immunosuppressive effects of Echinodorus macrophyllus aqueous extract. Journal of Ethnopharmacology. Nov. 28, 2006;111(2):435-9.
Robbins et al., Regulation of immune responses by extracellular vesicles. Nat Rev Immunol. 2014; 14(3):195-208.
Robbins et al., siRNA and innate immunity, Oligonucleotides 2009; 19(2):89-102.
Robbins, M. Misinterpreting the therapeutic effects of small interfering RNA caused by immune stimulation. Hum Gen Ther. 2008;19(10):991-9.
Romano et al., MiR-494 is regulated by ERK1/2 and modulates TRAIL-induced apoptosis in non-small-cell lung cancer through BIM down-regulation. Proc Natl Acad Sci U S A. Oct. 9, 2012;109(41):16570-5.
Sandhu et al., miR-155 targets histone deacetylase 4 (HDAC4) and impairs transcriptional activity of B-cell lymphoma 6 (BCL6) in the Eµ-miR-155 transgenic mouse model. Proc Natl Acad Sci USA. Dec. 4, 2012;109(49):20047-52.
Schiffelers, R. Cancer siRNA therapy by tumor selective delivery with ligand-targeted sterically stabilized nanoparticle. Nucleic Acids Res. Nov. 1, 2004;32(19):e149.
Schwab et al., Highly specific gene silencing by artificial microRNAs in *Arabidopsis*. The Plant Cell. 2006;18:1121-33.
Sharma et al., Recent advances in plant-virus interaction with emphasis on small interfering RNAs (siRNAs). Mol Biotechnol. 2013;55:63-77.
Sioud, M. Induction of inflammatory cytokines and interferon responses by double-stranded and single-stranded siRNA is sequence-dependent and requires endosomal localization. J Mol Biol. 2005;348(5):1079-90.
Sledz et al., Activation of the interferon system by short-interfering RNAs. Nat Cell Biol. 2003;5:834.
Stoorvogel, W. Functional transfer of microRNA by Exosomes. Blood. 2012;119:646-8.
Swiatczak et al., How the interplay between antigen presenting cells and microbiota tunes host immune responses in the gut. Semin Immunol. Feb. 2012;24(1):43-9.
Taganov et al., NF-kappaB-dependent induction of microRNA miR-146, an inhibitor targeted to signaling proteins of innate immune responses. Proc Natl Acad Sci USA. 2006;103:12481-6.
Tatematsu et al., Beyond dsRNA: Toll-like receptor 3 signalling in RNA-induced immune responses. Biochem J. 2014;458(2):195-201.
Tian et al., Dynamics of exosome internalization and trafficking. J Cell Physiol. 2013;228:1487-95.
Valadi et al., Exosome-mediated transfer of mRNA and microRNA is a novel mechanism of genetic exchange between cells. Nat Cell Biol. 2007;9:654-9.
van der Grein et al., "Small Talk" in the innate immune system via RNA-containing extracellular vesicles. Front Imm. 2014;5:542.
Vaucheret et al., Ingested plant miRNAs regulate gene expression in animals. Cell Research. Oct. 25, 2011;22(1):3-5.
Witwer et al., Transfer and functional consequences of dietary microRNAs in vertebrates: Concepts in search of corroboration. BioAssay. 2014;36(4):394-406.
Xiao et al., MiR-150 controls B cell differentiation by targeting the transcription factor c-Myb. Cell 2007;131:146-59.

(56) References Cited

OTHER PUBLICATIONS

Xie et al., DICER-LIKE 4 functions in trans-acting small interfering RNA biogenesis and vegetative phase in *Arabidopsis thaliana*. Proc Natl Acad Sci USA. 2005;102:12984-9.
Xie et al., Genetic and functional diversification of small RNA pathways in plants. PLoS Biol. May 2004;2(5):E104.
Yu et al., Toll-like receptor 3, RIG-I-like receptors and the NLRP3 inflammasome: Key modulators of innate immune responses to double-stranded RNA viruses. Cytokine and Growth Factor Reviews. Apr. 3, 2011;22(2):63-72.
Zhan et al., Functional regulation of monocyte-derived dendritic cells by microRNAs. Protein Cell. Jul. 2012;3(7):497-507.
Zhang et al., Analysis of plant-derived miRNAs in animal small RNA datasets. BMC Genomics. Aug. 8, 2012;13:381.
Zhang et al., Exogenous plant MIR168a specifically targets mammalian LDLRAP1: evidence of cross-kingdom regulation by microRNA. Cell Research. 2012;22:107-26.
Kim et al., Effective delivery of anti-miRNA DNA oligonucleotides by functionalized gold nanoparticles. J Biotechnol. Sep. 20, 2011;155(3):287-92.
Rosas-Cardenas et al. (Feb. 24, 2011) "A simple and efficient method for isolating small RNAs from different plant species," Plant Methods. 7(4):1-7.
European Search Report for Application No. EP 15720695.4, dated Nov. 15, 2017. (6 Pages).
Brown, et al., "Endogenous microRNA can be broadly exploited to regulate transgene expression according to tissue, lineage and differentiation state", Nature Biotechnology, 2007, 25(12): 1457-1467.
Calabrese, et al., "RNA sequence analysis defines Dicer's role in mouse embryonic stem cells", PNAS, 2007, 104(46): 18097-18102.
Elmesmari, et al., "MicroRNA-155 regulates monocyte chemokine and chemokine receptor expression in Rheumatoid Arthritis", Rheumatology, 2016, 55: 2056-2065.
Feng, et al., "Cardiac RNA Induces Inflammatory Responses in Cardiomyocytes and Immune Cells via Toll-like Receptor 7 Signaling", Journal of Biological Chemistry, 2015, 290(44): 26688-26698.
Feng, et al., "Extracellular MicroRNAs Induce Potent Innate Immune Responses via TLR7/MyD88-Dependent Mechanisms", Journal of Immunology, 2017, 199(6): 2106-2117.
Gilleron, et al., "Image-based analysis of lipid nanoparticle—mediated siRNA delivery, intracellular trafficking and endosomal escape", Nature Biotechnology, 2013, 31(7): 638-648.
He, et al., "Microvesicles containing miRNAs promote muscle cell death in cancer cachexia via TLR7", PNAS, 2014, 111(12): 4525-4529.
Janas, et al., "Alternative RISC assembly: Binding and repression of microRNA—mRNA duplexes by human Ago proteins", RNA, 2012, 18: 2041-2055.
Jin, et al., "Transfection of microRNA Mimics Should Be Used with Caution", Frontiers in Genetics, 2015, 6(340): 1-23.
Kim, et al., "Identification of a Novel Toll-like Receptor 7 Endogenous Ligand in Rheumatoid Arthritis Synovial Fluid That Can Provoke Arthritic Joint Inflammation", Arthritis & Rheumatology, 2016, 68(5): 1099-1110.
Kleinman, et al., "Sequence—and target-independent angiogenesis suppression by siRNA via TLR3", Nature, 2008, 452:591-598.
Kleinman, et al., "Short-interfering RNAs Induce Retinal Degeneration via TLR3 and IRF3", Molecular Therapy, 2012, 20(1): 101-108.
Kuchen, et al., "Regulation of MicroRNA Expression and Abundance during Lymphopoiesis", Immunity, 2010, 32: 828-839.
Kurowska-Stolarska, et al., "MicroRNA-155 as a proinflammatory regulator in clinical and experimental arthritis", PNAS, 2011, 108(27): 11193-11198.
Lehmann, et al., "An unconventional role for miRNA: let-7 activates Toll-like receptor 7 and causes neurodegeneration", Nature Neuroscience, 2012, 15(6): 827-837.
Liang, et al., "Extracellular microRNAs initiate immunostimulation via activating toll-like receptor signaling pathways", ExRNA, 2019, 1(9): 1-5.
Mullokandov, et al., "High-throughput assessment of microRNA activity and function using microRNA sensor and decoy libraries", Nature Methods, 2012, 9(8): 840-848.
Neilson, et al., "Dynamic regulation of miRNA expression in ordered stages of cellular development", Genes & Development, 2007, 21: 578-589.
Ranganathan, et al., "Serum miR-29a Is Upregulated in Acute Graft-versus-Host Disease and Activates Dendritic cells through TLR Binding", Journal of Immunology, 2017, 198: 2500-2512.
Salvi, et al., "Exosome-delivered microRNAs promote IFN-a secretion by human plasmacytoid DCs via TLR7", JCI Insight, 2018, 3(10): 1-12.
Sarvestani, et al., "Sequence-dependent off-target inhibition of TLR7/8 sensing by synthetic microRNA inhibitors", Nucleic Acids Research, 2014, 42(2): 1177-1188.
Xu, et al., "Circulating Plasma Extracellular Vesicles from Septic Mice Induce Inflammation via MicroRNA—and TLR7—Dependent Mechanisms", Journal of Immunology, 2018, 1-9.
Yelamanchili, et al., "MiR-21 in Extracellular Vesicles Leads to Neurotoxicity via TLR7 Signaling in SIV Neurological Disease", PLOS Pathogens, 2015, 1-22.
Zhang et al., "TLR8 and its endogenous ligand miR-21 contribute to neuropathic pain in murine DRG", Journal of Experimental Medicine, 2018, 215(12): 3019-3037.
Zitzer, et al., "Toll-Like Receptor Stimulation by MicroRNAs in Acute Graft-vs.-Host Disease", Frontiers in Immunology, 2018, 9: 1-7.
Colizzi (Mar. 8, 2014) "Nuovi integratori vegetali e Alimenti Funzionali: it caso della Moringa oleifera, pianta tropicale officinale," Aula Magna. 1-43. Accessible on the Internet at URL: https://www.vglobale.it/wp-content/uploads/2014/03/8Marzo-Colizzi-Moringa.pdf.
Hornung et al. (2005) "Sequence-specific potent induction of IFN-α by short interfering RNA in plasmacytoid dendritic cells through TLR7," Nature Medicine. 11(3):263-270.
Wagner et al. (2015) "Food derived microRNAs," Food & Function. 6(3):714-718.

\* cited by examiner

FIG. 2

A

```
                       U      ACme
5'     UUGACAG AAGAGAG GAGC      3'  FvmiR156   (SEQ ID NO:1)
       IIIIII  IIIIIIo IIII
3' meUCACUGUC UUCUCUU CUCG       5'  FvmiR156*  (SEQ ID NO:2)
           U       U    A
```

B

```
            C           U
5'     UCG UUGGUGCAGG CGGGAAme  3'  FvmiR168   (SEQ ID NO:3)
       IIo IIIoIIIIoI IIII
3' meUAAGU AACUACGUUC GCCC       5'  FvmiR168*  (SEQ ID NO:4)
            C           C
```

C

```
                AU        Cme
5'     UCGCUUGGUGCAG CGGGA       3'  OsamiR168  (SEQ ID NO:5)
       IIoIIIIIIIIIo IIIII
3' meUAAGUGAACCACGUU GCCCU       5'  OsamiR168* (SEQ ID NO:6)
                CC        AG
```

D

```
5'    AGAACGGCAUCAAAGCCAACU  3' sgfp   (SEQ ID NO:7)
      IIIIIIIIIIIIIIIIIIII
3'    UUUCUUGCCGUAGUUUCGGUU  5' asGFP  (SEQ ID NO:8)
```

PLANT SRNA EXTRACT OR PLANT MIRNA FOR USE AS AN IMMUNOSUPPRESSIVE AGENT

CROSS-REFERENCES TO RELATED APPLICATIONS

This application is a national stage application, filed under 35 U.S.C. § 371, of International Application No. PCT/EP2014/058888, filed on Apr. 30, 2014, the content of which is incorporated herein by reference in its entirety and for all purposes.

INCORPORATION BY REFERENCE OF SEQUENCE LISTING

The content of the text file named "49839_505N01US_SL.txt," which was created on Oct. 27, 2016 and is 2.12 KB in size, is hereby incorporated herein by reference in its entirety.

The present invention relates to a plant sRNA extract for use as an immunosuppressive agent. The present invention further relates to plant miRNA for use as an immunosuppressive agent.

In a further embodiment, the present invention relates to plant miRNA for use as an anti-inflammatory agent.

A wide variety of eukaryotic organisms, including plants, animals, and fungi, have evolved several RNA-silencing pathways to protect their cells and genomes against invading nucleic acids, such as viruses or transposons, and to regulate gene expression during development or in response to external stimuli (for review, see Baulcombe (2005) Trends Biochem. Sci. 30: 290-293; Meins et al. (2005) Annu. Rev. Cell Dev. Biol. 21:297-318).

The discovery of microRNAs (miRNAs) is one of the major scientific breakthroughs in recent years. These small non-coding RNA are changing the way of thinking about the development of the immune system and regulation of immune functions (for a review see Bi Y. et al.; MicroRNAs: novel regulators during the immune response. J Cell Physiol. 2009 March; 218(3):467-72; O'Connell R. M. et al.; Physiological and pathological roles for microRNAs in the immune system. Nat Rev Immunol. 2010 February; 10(2): 111-22). Endogenous miRNAs have been proposed as therapeutics or targets in the cure of cancer and other disorders (Calin G. A and Croce C M; MicroRNA signatures in human cancers. Nat Rev Cancer. 2006 November; 6(11):857-66).

Recently in addition to the known effects of intracellular or intraspecific miRNAs a more profound change of paradigm has been proposed by the appearance of evidences that indicate the potential of plant miRNAs to modulate human cells (Zhang L et al., Exogenous plant MIR168a specifically targets mammalian LDLRAP1: evidence of cross-kingdom regulation by microRNA. Cell Research, 2012 22:107-126). In a recent highly debated report, Zhang et al (supra) discovered that the specific rice MIR168a could specifically target the mammalian low-density lipoprotein receptor adapter protein, decreasing its expression in liver with consequence on LDL levels. If validated, diet-derived foreign microRNA absorption and function in consuming vertebrates would drastically alter our understanding of nutrition and ecology. Therapeutic exploitation of RNAi in treating human disease is difficult because these accessory processes are absent or diminished in most animals. A recent report challenged multiple paradigms, suggesting that ingested microRNAs (miRNAs) are transferred to blood, accumulate in tissues, and exert canonical regulation of endogenous transcripts (see review by Witwer and Hirsch (2014), Transfer and functional consequences of dietary microRNAs in vertebrates: Concepts in search of corroboration, BioAssays).

In plants, RNA-silencing pathways have been shown to control a variety of developmental processes including flowering time, leaf morphology, organ polarity, floral morphology, and root development (reviewed by Mallory and Vaucheret (2006), Nat, Genet, 38:S31-36). All RNA-silencing systems involve the processing of double-stranded RNA (dsRNA) into small RNAs of 21 to 25 nucleotides (nt) by an RNaseIII-like enzyme, known as Dicer or Dicer-like in plants (Bernstein et al. (2001) Nature 409: 363-366; Xie et al. (2004) PLoS Biol 2, E104:0642-0652; Xie et al. (2005) Proc Natl Acad Sci USA 102: 12984-12989; Dunoyer et al., (2005) Nat Genet 37: 1356-1360). These small RNAs are incorporated into silencing effector complexes containing an Argonaute protein (for review, see Meister and Tuschl (2004) Nature 431: 343-349).

There are a number of major differences between plant and animal miRNA: Plant microRNA precursors are transcribed by RNA polymerase II as in animals. However, in contrast to animals the entire process of plant microRNA biogenesis is undertaken within the plant nucleus. The mature microRNAs are exported out of the nucleus by Hasty, an exportin 5-like protein found in plants. There are fundamental differences between plant and animal microRNAs (Axtell, M J., et al. Vive la difference: biogenesis and evolution of microRNAs in plants and animals. Genome Biology. 12(2011): p. 221-234.):

a) In animals miRNA precursors are sequentially processed by Drosha followed by Dicer to produce miRNA duplexes whereas only one Dicer-like enzyme (DCL1) is required in plants.

b) In plants miRNA duplexes are methylated at the 2'OH group at the 3' termini.

c) The target recognition process between plants and animals is different. In plants miRNAs direct mRNA cleavage of a microRNA target whereas in animals miRNAs usually inhibit translation of their targets.

d) In contrast to the nearly perfect match of plant miRNAs to the exons of their target, hybridization of microRNA to targets in animals is less stringent and only a canonical 7-8 nucleotide "seed sequence" is known to be specific for microRNA target recognition.

Studies focus on the role of plant miRNAs in plant; e.g. by the development of artificial miRNAs. Artificial microRNAs (amiRNAs) have been described in *Arabidopsis* targeting viral mRNA sequences (Niu et al. (2006) Nature Biotechnology 24: 1420-1428) or endogenous genes (Schwab et al. (2006) Plant Cell 18: 1121-1133). The amiRNA construct can be expressed under different promoters in order to change the spatial pattern of silencing (Schwab et al. (2006) Plant Cell 18: 1121-1133). Artificial miRNAs replace the microRNA and its complementary star sequence in a miRNA precursor backbone and substitute sequences that target an mRNA to be silenced.

Silencing by endogenous miRNAs can be found in a variety of spatial, temporal, and developmental expression patterns (Parizotto et al. (2007) Genes Dev 18:2237-2242; Alvarez et al. (2006) Plant Cell 18: 1134-51).

As plant miRNAs are known to target plant target sequences, the effect of plant miRNAs in animals is unknown.

Immune-related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases such as rheumatoid arthritis, immune mediated renal disease, hepatobiliary diseases, inflammatory bowel disease (IBD), psoriasis, and asthma, and non-immune-mediated inflammatory diseases, infectious diseases, immunodeficiency diseases, neoplasia, etc. However, there is still a need for treatments of inflammatory diseases, which are more efficient and/or exhibit fewer side effects than known treatments. The same applies for methods of preventing such diseases.

siRNAs have been proposed as a potential break-through in therapy of cancer and other human diseases (Schiffelers R M 2004 NAR). The main limiting step to this therapeutic application is that canonical siRNA duplexes are potent activators of the mammalian innate immune system (Robbins et al., Oligonucleotides 2009) and therefore show undesired off-effects such as their induction of pro-inflammatory processes (Homung V et al, Nat Med 2005; Judge A D et al Nat Biotechnol 2005; Sloud M, J Mol Biol, 2005).

Other recent discoveries have shown that both high molecular weight dsRNA and siRNA induce inflammation triggering Toll-like receptor signalling (Tatematsu M, Seya T, Matsumoto M. (2014). Beyond dsRNA: Toll-like receptor 3 signalling in RNA-induced immune responses. Biochem J., 1; 458(2): 195-201; Homung V et al, Nat Med 2005; Judge A D et al Nat Biotechnol 2005; Sloud M, J Mol Biol, 2005).

Dendritic cells are the best known integrators of external signals, they insert their dendrites within epithelial cells in Peyer's patches, just before the ileo-caecal valve, to sense microorganisms (Swiatczak B, Rescigno M. How the interplay between antigen presenting cells and microbiota tunes host immune responses in the gut. Semin Immunol. 2012 February; 24(1):43-9). dsRNAs and potentially miRNA are likely recognized as a viral threat and therefore would be expected to elicit a pro-inflammatory response rather than the surprising anti-inflammatory response that we report.

Therefore, plant miRNAs targeting beneficial gene regulatory process through specified food intake (i.e probiotics, specific diet regime) will likely be sensed by DCs trough specific mechanisms from the same receptors but in a different manner than viral and human miRNAs (Croce et al., 2012 PNAS) Also, DC master regulators of immune response modulated inflammation and tolerance by interacting with T cells directly or through cytokine production.

Human internally produced miRNAs are normally implicated in establishing and maintaining the cell fate of immune cells (e.g. miR-155 (O'Connell R. M. et al; MicroRNA-155 promotes autoimmune inflammation by enhancing inflammatory T cell development. Immunity. 2010), miR-181a (Li Q J et al, 2007. miR-181a is an intrinsic modulator of T cell sensitivity and selection. Cell 129:147-161), miR-150 (Xiao C et al. 2007. MiR-150 controls B cell differentiation by targeting the transcription factor c-Myb. Cell 131:146-159), miR-223 (Johnnidis J B et al., 2008. Regulation of progenitor cell proliferation and granulocyte function by microRNA-223. Nature 451:1125-1129) and miR146 (Taganov K D et al., NF-kappaB-dependent induction of microRNA miR-146, an inhibitor targeted to signaling proteins of innate immune responses. Proc Natl Acad Sci USA 2006; 103: 12481-6.).

Thus, in one embodiment, the present invention relates a plant sRNA extract for use as an immunosuppressive agent.

Surprisingly, it was found that plant sRNA extract and plant miRNAs exhibit an anti-inflammatory effect, as opposed to what was observed for canonical siRNAs and exogenously supplied mammalian miRNAs (Croce et al. 2012 PNAS). Surprisingly, it could be shown that administering plant sRNA extract and/or plant miRNA in conjunction with different inflammatory agents, dampens inflammation per se and also prevents inflammation.

Therefore, the experiments surprisingly show that plant sRNA extracts and plant miRNA are effective as anti-inflammatory agents, which can attenuate T cell proliferation and production both of inflammatory cytokines and co-stimulatory molecules in stimulated human dendritic cells, as described in the Examples.

This result shows a profound functional difference of plant miRNA as compared to human miRNA, i.e an opposite role in immuno-modulatory properties. Therefore, plant sRNA extracts and plant miRNA exhibit unique, unexpected properties.

According to the present invention, a "plant sRNA extract" is understood as a composition comprising plant material of a given plant variety wherein the amount of sRNA of said plant variety in comparison to other RNA of the same plant variety in said composition is higher than in naturally occurring plant material of said plant variety.

In a preferred embodiment, the "plant sRNA extract" is understood as a composition comprising plant material of a given plant variety wherein the amount of sRNA of said plant variety in comparison to other RNA of the same plant variety in said composition is at least 10% higher than in naturally occurring plant material of said plant variety, more preferably at least 20%, 50%, 100% or 200% higher than in naturally occurring plant material of said plant variety.

Typically, the amount is determined as (w/v) or (w/w).

In more preferred embodiment, the "plant sRNA extract" according to the present application refers to the purified small RNA fraction of a plant optionally dissolved in a suitable solvent. The plant miRNA extract when dissolved in a suitable solvent comprises less than 20% (w/v), preferably less than 10% (w/v), more preferably less than 5% (w/v), even more preferably less than less than 1% (w/v) of other plant components, in particular other RNA. A suitable solvent is preferably an aqueous solution, which is more preferably a buffered aqueous solution, which may comprise further substance like RNAse inhibitors.

In case the extract is not dissolved, the extract may be solid, for example it may be a dry, dried, or freeze-dried extract. Also, the extract may be in the form of a liquid or frozen fluid, such as a solution, suspension, dispersion, or the extract may be in the form of a gel.

For extraction from plant, a complete plant or parts thereof of may be used. Preferably, plant sRNA may be extracted from leaves, flowers, roots, fruits, seeds or parts thereof. In particular strawberry fruits may be used.

The plant or parts thereof are preferably ground or shredded prior to extraction. For example, the plant or parts thereof may be pulverized, in particular in liquid nitrogen as described in Example 1.

In another preferred embodiment, the "plant sRNA extract" according to the present application refers to the purified small RNA fraction of a plant optionally dissolved in a suitable solvent. The plant miRNA extract when dissolved in a suitable solvent comprises less than 20% (w/v), preferably less than 10% (w/v), more preferably less than 5% (w/v), even more preferably less than less than 1% (w/v) of other plant components.

According to the present invention, the term "plant" encompasses any member of the plant-kingdom according to the Linnaeus definition, encompassing both vascular and non-vascular plants.

In a preferred embodiment of the extract for use of the present invention, the sRNA has a length of 200 nucleotides or less, preferably a length of 120 nucleotides or less, preferably a length between 10 and 120 nucleotides.

Therefore, in a preferred embodiment, the "sRNA plant extract" comprises the sRNA of a plant which has a length of 200 nucleotides or less, preferably a length of 120 nucleotides or less, preferably a length between 10 and 120 nucleotides.

In an even more preferred embodiment, the sRNA has a length of 10 nucleotides or more.

Therefore, in a preferred embodiment, the "sRNA plant extract" comprises the sRNA of a plant which has a length of 10 nucleotides or more.

Thus, in an even more preferred embodiment of the present invention, the sRNA has a length of between 10 and 200 nucleotides, preferably a length of between 10 and 160 nucleotides, more preferably a length of between 10 and 120 nucleotides, even more preferably a length of between 10 and 100 nucleotides, even more preferably a length of between 10 and 50 nucleotides, most preferably a length of between 10 and 25 nucleotides. Therefore, in yet a further preferred embodiment, the "sRNA plant extract" comprises the sRNA of a plant which has a length of between 10 and 200 nucleotides, preferably a length of between 10 and 160 nucleotides, more preferably a length of between 10 and 120 nucleotides, even more preferably a length of between 10 and 100 nucleotides, even more preferably a length of between 10 and 50 nucleotides, most preferably a length of between 10 and 25 nucleotides.

The sRNA fraction extracted from plants containing the sRNA of a plant which has a length of between 10 and 25 nucleotides corresponds to the miRNA fraction. Therefore, this sRNA plant extract is particularly preferred.

"sRNA" according to the present invention is small RNA, in particular RNA of a length of 200 nucleotides or less.

In a further preferred embodiment, the sRNA does not contain ribosomal RNA, or contains less than 70%, 50%, 10%, 10% or 1% ribosomal RNA (rRNA) of the same plant variety. For example, the ribosomal RNA is 5S rRNA, 5.8S rRNA, 18S rRNA, or 28S rRNA.

Therefore, in a yet further preferred embodiment, the sRNA has a length of length of 120 nucleotides or less, preferably a length between 10 and 120 nucleotides.

In a preferred embodiment of the extract for use of the invention, the sRNA is miRNA.

In a further embodiment, the present invention relates to miRNA for use as an immunosuppressive agent.

In a further embodiment, the present invention relates to a plant sRNA extract as defined above or plant miRNA for use in a method for treating and/or preventing an inflammatory disease.

As used herein the term "inflammatory disease" and/or "inflammation", used interchangeably, includes inflammatory abnormalities characterized by enhanced immune response to harmful stimuli, such as pathogens, damaged cells, or irritants. Inflammatory diseases underlie a vast variety of human diseases.

In a preferred embodiment, the inflammatory disease is selected from the group consisting of chronic prostatitis, Glomerulonephritis, Hypersensitivities, Pelvic inflammatory disease, Reperfusion injury, Sarcoidosis, Vasculitis, Interstitial cystitis, normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

In a further preferred embodiment, said inflammatory disease is an autoimmune disease.

In a particularly preferred embodiment, said autoimmune disease is selected from the group consisting of multiple sclerosis, rheumatoid arthritis; psoriatic arthritis, discoid lupus erythematosus, systemic lupus erythematosus (SLE); ulcerative colitis; Crohn's disease; benign lymphocytic angiitis, autoimmune lymphoproliferative syndrome, sarcoidosis, autoimmune thrombocytopenic purpura, idiopathic thrombocytopenic purpura, pure red cell aplasia, Sjogren's syndrome, rheumatic disease, polymyalgia rheumatica, mixed connective tissue disease, inflammatory rheumatism, degenerative rheumatism, extra-articular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, ANCA-associated vasculitis, temporal arteritis, giant cell arteritis, Takayasu arteritis, Behcet's disease, antiphospholipid syndrome, myasthenia gravis, autoimmune haemolytic anemia, Guillain-Barre syndrome, chronic immune polyneuropathy, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, Hashimoto's thyroiditis, fibromyalgia, chronic fatigue and immune dysfunction syndrome (CFIDS), primary myxedema, sympathetic ophthalmia, autoimmune inner ear disease, autoimmune uveitis, autoimmune chronic active hepatitis, collagen diseases, ankylosing spondylitis, periarthritis humeroscapularis, panarteritis nodosa, polyarteritis nodosa, chondrocalcinosis, Wegener's granulomatosis, microscopic polyangiitis, chronic urticaria, bullous skin disorders, pemphigoid, bullous pemphigoid, cicatricial pemphigoid, vitiligo, atopic eczema, eczema, chronic urticaria, autoimmune urticaria, normocomplementemic urticarial vasculitis, hypocomplementemic urticarial vasculitis, alopecia areata, alopecia universalis, alopecia totalis, Devic's disease, pernicious anemia, childhood autoimmune hemolytic anemia, idiopathic autoimmune hemolytic anemia, refractory or chronic Autoimmune Cytopenias, Prevention of development of Autoimmune Anti-Factor VIII Antibodies in Acquired Hemophilia A, Cold agglutinin disease, Neuromyelitis Optica, Stiff Person Syndrome, gingivitis, periodontitis, pancreatitis, myocarditis, gastritis, gout, gouty arthritis, idiopathic pericarditis, anti-synthetase syndrome, scleritis, macrophage activation syndrome, PAPA Syndrome, Blau's Syndrome, adult and juvenile Still's disease, cryopyrin associated periodic syndrome, Muckle-Wells syndrome, familial cold auto-inflammatory syndrome, neonatal onset multisystem inflammatory disease, chronic infantile neurologic cutaneous and articular syndrome, familial Mediterranean fever, Hyper IgD syndrome, Schnitzler's syndrome, autoimmune retinopathy, age-related macular degeneration, and TNF receptor-associated periodic syndrome (TRAPS).

In a yet further preferred embodiment, the inflammatory disease is an allergic disease.

In a particularly preferred embodiment, said allergic disease is selected from the group consisting of
a) allergic respiratory disease, such as bronchial asthma, pediatric asthma, allergic asthma, atopic asthma, aspirin asthma, or allergic bronchitis,
b) allergic nasal disease, such as allergic rhinitis, vernal catarrh, hay fever, or chronic allergic rhinitis,
c) an allergic skin disease, such as atopic dermatitis,
d) an allergic ocular disease, such as hay fever, seasonal allergic conjunctivitis, or chronic allergic conjunctivitis,
e) hypersensitivity pneumonitis,
f) contact dermatitis, and
g) food allergy.

In a further preferred embodiment, said inflammatory disease is psoriasis.

In a further preferred embodiment, said inflammatory disease is inflammatory bowel disease, more preferably Crohn's disease or ulcerative colitis.

In a further preferred embodiment, said inflammatory disease is ulcerative colitis.

As used herein, "inflammatory bowel disease" also refers to a related disease and refers to all types and stages of inflammatory bowel disease (IBD), including, but not limited to: Crohn's disease and ulcerative colitis (UC). Optionally, conditions relating to IBD include, e.g., Collagenous colitis, Lymphocytic colitis, Ischaemic colitis, Diversion colitis, Behcet's disease, Indeterminate colitis.

As used herein, "psoriasis" also refers to a related disease and refers to all types and stages of psoriasis, including, but not limited to: Nonpustular Psoriasis including Psoriasis vulgaris and Psoriatic erythroderma (erythrodermic psoriasis), Pustular psoriasis including Generalized pustular psoriasis (pustular psoriasis of von Zumbusch), Pustulosis palmaris et plantaris (persistent palmoplantar pustulosis, pustular psoriasis of the Barber type, pustular psoriasis of the extremities), Annular pustular psoriasis, Acrodermatitis continua, Impetigo herpetiformis. Optionally, conditions relating to psoriasis include, e.g., drug-induced psoriasis, Inverse psoriasis, Napkin psoriasis, Seborrheic-like psoriasis, Guttate psoriasis, Nail psoriasis, Psoriatic arthritis.

In the Examples, it is shown that plant sRNA extracts and plant miRNAs attenuate T cell proliferation and the expression and/or production of IL-1β, TNFα, CD80, CD86 and CD83 of stimulated dendritic cells. Therefore, plant sRNA extracts and plant miRNAs are in particular useful in the treatment and/or prevention of autoimmune diseases or inflammatory diseases, in which IL-1β, TNFα, CD80, CD86 and/or CD83 play a role, and/or wherein dendritic cells are dysregulated. For example in patients with Crohn's disease, pro-inflammatory Th17 and Th1 cytokines outweigh the effect of anti-inflammatory cytokines secreted by regulatory T cells (Treg). This results in an imbalance of pro-inflammatory and anti-inflammatory cytokines. Thus, Crohn's disease may be treated and/or prevented with plant miRNA according to the present invention.

Thus, in a further preferred embodiment, the inflammatory disease is characterized by an increase in CD4$^+$ T cell proliferation.

Thus, in a further preferred embodiment, the inflammatory disease is characterized by an increase in expression or production of at least one of inflammatory biomarker, in particular selected from IL-1β and TNFα and/or wherein the inflammatory disease is characterized by a dysregulation of the cytokines or co-receptors in at least, and/or by a dysregulation of immune function as detectable in changing of DC activity (i.e. costimulatory molecules expression).

Thus, in a further preferred embodiment, the inflammatory disease is characterized by an increase in expression or production of IL-10, such as lymphoma, in particular non-Hodgkin's lymphoma, and Burkitt lymphoma, melanoma and non-small cell lung cancer.

A "patient" is understood as animal, in particular a human in need of treatment and/or prevention. Accordingly, the plant sRNA extract or plant miRNA for use in prevention and/or treatment is suitable for the prevention and/or treatment of animals, in particular humans in need of treatment and/or prevention.

As shown in the Examples, plant sRNA extracts from monocot and dicot plants are effective in attenuating the T cell proliferation.

Surprisingly, the total sRNA extract from strawberry, namely *Fragaria vesca*, is even more effective.

Thus, the sRNA extract for use may be from any plant, in particular from a monocot or dicot. For example, plant sRNA extracted from soybean, maize, or strawberry may be used.

In a preferred embodiment of the plant sRNA extract or plant miRNA for use of the invention, the plant is a flowering plant.

In a more preferred embodiment of the plant sRNA extract or plant miRNA for use of the invention, the plant is a *Rosacea* spp.

*Rosaceae* plants are known to a skilled person in include the subfamily Rosoideae, in particular rose, blackberry, raspberry, strawberry, *Potentilla* and *Geum*; the subfamily Amygdaloideae, in particular pome fruits, traditionally known as subfamily Maloideae or Pyroideae, like apple, cotoneaster, and hawthorn; the Spiraeoideae; and the subfamily Dryadoideae, in particular the genera *Dryas, Cercocarpus, Chamaebatia, Cowania*, and *Purshia*.

In an even more preferred embodiment of the plant sRNA extract or plant miRNA for use of the invention, the plant is a strawberry, most preferred *Fragaria vesca*.

In a yet further preferred embodiment, one or more different plant sRNA extracts and/or plant miRNAs are administered. For example 2, 3, 4, 5, 6, 7, 8, 9 or 10 different plant sRNA extracts may be administered. For example, sRNA extracts from strawberry and soybean may be administered.

The one or more different plant sRNA extracts may be administered together or separately, or they may be administered simultaneously, or at different time points.

Moreover, some synthetic specific plant miRNAs are effective in attenuating T cell proliferation and the expression and/or production of inflammatory cytokines IL-1β, TNFα, and immune reactivity of stimulated dendritic cells by means of CD80, CD86 and CD83 proper expression. A synthetic miRNA is understood as a miRNA which exists naturally in a plant, which is obtained by chemical synthesis. Alternatively, the specific plant miRNAs may be purified from plants. The synthesis of miRNA is known in the art and is for example described in Example 1.

The plant miRNA for use of the invention is preferably a purified miRNA.

A purified plant miRNA typically contains less than 10%, 1%, 0.01% or 0.001% of other components, in particular plant components.

The one or more different plant miRNAs may be administered together or separately, or they may be administered simultaneously, or at different time points.

Preferably, at least one plant sRNA extract and/or two or more purified miRNAs are administered.

Surprisingly, miR168 from *Fragaria vesca* is highly effective regarding its immunosuppressive effect, as shown in the examples. Thus, in a preferred embodiment, the plant miRNA for use according to the invention is *F. vesca* miR168.

In particular, plant sRNA extracts from one plant or more than one plant may be administered. For example plant sRNA extracts from two different plant varieties or different plant families may be administered.

"More than one" is understood to encompass for example 2, 3, 4, 5, 6, 7, 8, 9, 10, 11, 12, 13, 14, 14, 20, 40 or more.

Plant sRNA extracts can be obtained as described in the Examples.

In a further preferred embodiment, the two or more plant sRNA extracts may be administered as a mixture of plant sRNA extracts. In particular, plant sRNA extracts from two different plant varieties or different plant families may be mixed and may be administered thereafter.

The plant sRNA extracts preferably contain methylated miRNAs or the miRNAs of the extract are methylated. In a further preferred embodiment, a plant miRNA for use is a methylated miRNA. A methylated miRNA for use according to the invention is preferably methylated at the 2'OH group of the 3' terminus.

The miRNAs for use according to the invention may be produced recombinantly using miRNA expression constructs, using methods known in the art (Schwab, R., Ossowski, S., Riester, M., Warthmann, N., and Weigel, D. (2006). Highly specific gene silencing by artificial microRNAs in *Arabidopsis*. The Plant Cell 18, 1121-1133), or may be isolated from plants.

Preferably, mature miRNA molecules are administered.

A number of miRNAs are described in the prior art and may be used according to the invention. These miRNAs are described in a large number of plant species as shown in Table 1 below (Kozomara, A., and Griffiths-Jones, S. (2011). miRBase: integrating microRNA annotation and deep-sequencing data. Nucleic Acids Research 39, D152-D157). These miRNAs were also described in *Fragaria ananassa* (Ge, A., Shangguan, L., Zhang, X., Dong, Q., Han, J., Liu, H., Wang, X., and Fang, J. (2012). Deep sequencing discovery of novel and conserved microRNAs in strawberry (*Fragaria×ananassa*). *Physiologia Plantarum*).

TABLE 1

| miRNA | Target sequence | Cleaved Genes |
|---|---|---|
| miR156/157 (12) | SQUAMOSA-promoter binding | SPL2, SPL3, SPL10 |
| miR158 (2) | Unknown | |
| miR159 (6) | MYB, TCP | MYB33, MYB65, TCP2, TCP3, TCP4, TCP10, TCP24 |
| miR160 (3) | ARF | ARF10, ARF17 |
| miR161 (1) | Pentatricopeptide repeat | At1g06580 |
| miR162 (2) | Dicer | DCL1 |
| miR163 (1) | Methyl transferases | |
| miR164 (3) | NAC-domain transcription factor | CUC1, CUC2, NAC1, At5g07680, At5g61430 |
| miR165/166 (9) | HD-ZIP transcription factor | PHB, PHV, REV, C3HDZIP1 |
| miR167 (4) | ARF | ARF8 |
| miR168 (2) | AGO | AGO1 |
| miR169 (14) | CCAAT-binding factor HAP2-like protein | At3g05690 |
| miR170/171 (4) | GRAS-domain transcription factor | SCL6-III, SCL6-IV |
| miR172 (5) | APETALA2-like transcription factor | AP2, TOE1, TOE2, TOE3 |
| miR173 (1) | Unknown | |
| miR393 (2) | Auxin receptors | TIR1, AFB1, AFB2, AFB3 |
| miR394 (2) | F-box protein | At1g27340 |
| miR395 (6) | ATP sulfurylase | APS4 |
| miR396 (2) | Growth-regulating-factor transcription factor Rhodenase-like protein, Kinesin-like protein | GRL1, GRL2, GRL3, GRL7, GRL8, GRL9 |
| miR397 (2) | Laccase, Beta-6 tubulin | At2g29130, At2g38080, At5g60020 |
| miR398 (3) | CSD, Cytochrome C oxidase subunit V | CSD1, CSD2, At3g15640 |
| miR399 (6) | Phosphate transporter | |

Preferably, miR156, miR *Rosacea* 168, osamiR168, or mixtures thereof are used.

A particularly preferred miRNA is miR168, in particular *Fragaria vesca* miR168.

A "miRNA" or "microRNA" for use according to the present invention is understood as oligoribonucleic acid, of about 19 to 24 nucleotides (nt) in length, which regulates expression of a polynucleotide comprising a target sequence. miRNAs are non-protein-coding RNAs and have been identified in both animals and plants. miRNAs are derived in plants via Dicer-like 1 processing of larger precursor polynucleotides. The term "miRNA" also encompasses "artificial miRNA", which comprise a miRNA sequence that is synthetically designed to silence a target sequence. In particular, such artificial miRNA exhibits 80% or more, preferably 90% or more, even more preferably 91%, 92%, 93%, 94%, 95%, 96%, 97%, 98%, 99% or more sequence identity with the nucleotide sequence of the unmodified miRNA or miRNA precursor backbone. In a preferred embodiment, the plant miRNA is methylated at the 2'OH group at the 3' terminus.

In a preferred embodiment, endogenous miRNAs are used, as the mechanism appears to be target-independent.

"miRNA precursor backbone" is a polynucleotide that provides the backbone structure necessary to form a hairpin RNA structure which allows for the processing and ultimate formation of the miRNA. Preferably, the backbone is from strawberry, rice, maize or soybean. microRNA precursor backbones have been described previously. For example, US20090155910A1 (WO 2009/079532) discloses the following soybean miRNA precursor backbones: 156c, 159, 166b, 168c, 396b and 398b, and US 20090155909A1 (WO 2009/079548) discloses the following maize miRNA precursor backbones: 159c, 164h, 168a, 169r, and 396h. Examples of miRNA precursor backbones include the miRNA GM-396b precursor backbone or active variants thereof and the miRNA GM-159 precursor backbone or active variants thereof, as described in WO 2012/154824.

A "miRNA expression construct" is understood as DNA construct which comprises a miRNA precursor backbone having a polynucleotide sequence encoding a miRNA and a star sequence. Such miRNA expression construct may be in a suitable vector, to allow expression in a suitable host, followed by isolation of the miRNA. Such expression systems are known to a skilled person and are for example described in (Schwab, R., Ossowski, S., Riester, M., Warthmann, N., and Weigel, D. (2006). Highly specific gene silencing by artificial microRNAs in *Arabidopsis*. The Plant Cell 18, 1121-1133) The plant miRNAs and plant sRNA extracts for use surprisingly exhibit anti-inflammatory activity. Such effect may be enhanced by combining the plant miRNAs or and plant sRNA extracts with other known anti-inflammatory agents.

Thus, in a further preferred embodiment, the plant sRNA extract or the plant miRNA for use of the invention is administered in combination with at least one other anti-inflammatory agent.

In a more preferred embodiment, said other anti-inflammatory agent is selected from the group consisting of a corticosteroid, a statin, interferon beta, a nonsteroidal anti-inflammatory drug (NSAID), methotrexate, Cyclosporin A and a disease-modifying anti-rheumatic drug (DMARD).

In another embodiment, the plant sRNA extract or the plant miRNA for use according to the invention is comprised in a pharmaceutical composition.

Thus, in a further embodiment, the present invention relates to a pharmaceutical composition comprising at least one plant miRNA or plant sRNA extract as defined herein, for use in a method for treating and/or preventing an inflammatory disease, as defined above.

In a preferred embodiment, the pharmaceutical composition comprises at least one plant miRNA or plant sRNA extract and at least one carrier. Carriers are generally known to those skilled in the art and include saline, sugars, polypeptides, polymers, lipids, creams, gels, micelle materials, and metal nanoparticles. In one more preferred embodiment, the carrier comprises at least one of the following: water, a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a liposome, a ligand functionalized cationic polymer, a ligand functionalized-hydrophilic polymer grafted polymer, and a ligand functionalized liposome. In another more preferred embodiment, the polymers comprise a biodegradable histidine-lysine polymer, a biodegradable polyester, such as poly(lactic acid) (PLA), poly(glycolic acid) (PGA), and poly(lactic-co-glycolic acid) (PLGA), a polyamidoamine (PAMAM) dendrimer, a cationic lipid, or a PEGylated PEI Cationic lipids include DOTAP, DOPE, DC-Chol/DOPE, DOTMA, and DOTMA/DOPE. In a yet further preferred embodiment, exosomes may be used. Such exosomes and their preparation are described e.g. in Montecalvo et al. (2012, Blood, 119: 756-766, and Stoorvogel, 2012, Blood, 119: 646-648). Further suitable pharmaceutical carriers are e.g. described in Remington's Pharmaceutical Sciences, supra, a standard reference text in this field. The pharmaceutical composition may further comprise conventional pharmaceutical additives and adjuvants, excipients or diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

A particularly preferred carrier is DOTAP, as used in the Examples.

Preferably, the pharmaceutical composition comprises at least one pharmaceutically acceptable RNAse inhibitor.

In still another embodiment, the carrier is a polymer, e.g. a histidine-lysine copolymer that forms a nanoparticle with the miRNA molecule(s). The diameter of the nanoparticle is about typically 100 nm to about 1000 nm.

The invention thus also provides a nanoparticle comprising one or more of the plant miRNA or plant sRNA extract for use of the invention. In an embodiment, the nanoparticle further comprises a carrier, such as one or more of those described herein, and optionally a targeting ligand.

In one further embodiment of the present invention, said plant miRNA or plant sRNA extract is comprised in a food additive or dietary supplement. Preferably, the dietary supplement, food additive, food or foodstuff comprises at least one RNAse inhibitor which is acceptable for such compositions. In particular, such RNAse inhibitor is not toxic.

Methods for determining the amount of sRNA or specific miRNA are known in the art. For example chip-based detection assays, like Agilent small RNA assays, or Millipore SmartRNAplex™ miRNA profiling assay, or PCR-based detection assays, like Qiagen miScript™ PCR System, TaqMan® MicroRNA Assays, or Exiqon miRCURY LNA™ Detection may be used.

Such food additive may be added to a food product, foodstuff, dietary supplement, nutritional supplement or a supplement composition for a food product or a foodstuff, for example beverages (e.g. but not limited to sports beverages, functional waters, juices, smoothies; instant drinks), soups, dairy products (e.g. but not limited to single shot yoghurt drinks), nutritional bars, and spreads, in particular beverages and nutritional bars.

For example, a *Fragaria vesca* sRNA extract may be prepared in liquid form such as an aqueous solution which optionally contains at least one RNAse inhibitor. Such solution can be used as food additive e.g. for beverages or dairy products. As used herein, the term food product refers to any food or feed suitable for consumption by humans or animals. The food product may be a prepared and packaged food (e.g., mayonnaise, salad dressing, bread, or cheese food) or an animal feed (e.g., extruded and pelleted animal feed, coarse mixed feed or pet food composition). As used herein, the term foodstuff refers to any substance fit for human or animal consumption. The term dietary supplement refers to a small amount of a compound for supplementation of a human or animal diet packaged in single or multiple dose units. Dietary supplements do not generally provide significant amounts of calories but may contain other micronutrients (e.g., vitamins or minerals). The term nutritional supplement refers to a composition comprising a dietary supplement in combination with a source of calories.

Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yoghurt and any other fat or oil containing foods, and food ingredients (e.g., wheat flour). The term food products or foodstuffs also includes functional foods and prepared food products, the latter referring to any pre-packaged food approved for human consumption.

The food products or foodstuffs may already contain RNA prior to the addition of a food additive comprising a plant miRNA or plant sRNA extract for use according to the invention. This may be the case for food products or foodstuff being, containing or derived from plants or parts thereof, such as fruits, or fruit juices.

In this embodiment, the resulting food products or foodstuffs contain an enlarged amount and/or concentration of plant miRNA or plant sRNA extract compared to the food products or foodstuffs without addition of such food additive.

In a preferred embodiment, such food products or foodstuffs contain an amount of plant sRNA which is at least 10% higher than the amount in the food product or foodstuff without addition of such food additive comprising a plant sRNA extract, more preferably the amount is at least 20%, 50%, 100% or 200% higher than in the food product or foodstuff without addition of such food additive comprising a plant sRNA extract.

In a further preferred embodiment, such food products or foodstuffs contain an amount of total plant miRNA which is at least 10% higher than the amount in the food product or foodstuff without addition of such food additive containing one or more specific miRNAs, more preferably the amount is at least 20%, 50%, 100% or 200% higher than in the food product or foodstuff without addition of such containing one or more specific miRNAs.

In a yet further preferred embodiment, such food products or foodstuffs contain an amount of a specific plant miRNA which is at least 10% higher than the amount of the specific plant miRNA in the food product or foodstuff without addition of such food additive containing one or more specific miRNAs, more preferably the amount is at least 20%, 50%, 100% or 200% higher than in the food product or foodstuff without addition of such containing one or more specific miRNAs.

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yoghurt, powder, suspension, chew, treat (e.g., biscuits) or any other delivery form.

Food compositions are preferably administered orally. Dietary supplements are preferably administered orally.

Therefore, in a yet further embodiment, the present invention relates to a food product comprising a plant sRNA extract or a plant miRNA as defined above.

Therefore, in a yet further embodiment, the present invention relates to a dietary supplement comprising a plant sRNA extract or a plant miRNA as defined above.

In a yet further embodiment, the present invention relates to a method for producing a second food product, comprising adding to a first food product a plant sRNA extract, or a plant miRNA as defined herein.

For example, a plant sRNA extract as defined above may be added to a beverage and may be mixed, resulting in a beverage containing or enriched with plant sRNA extract. In case the first food product does not contain plant sRNA, the second food product contains plant sRNA.

Therefore, the first food product is in a preferred embodiment a food product which does not contain plant sRNA and/or plant miRNA.

In another preferred embodiment, the first food product contains plant sRNA and/or plant miRNA. In one preferred embodiment, such second food product contain an amount of plant sRNA which is at least 10% higher than the amount in the first food product, more preferably the amount is at least 20%, 50%, 100% or 200% higher than in first food product.

In a further preferred embodiment, such second food product contains an amount of total plant miRNA which is at least 10% higher than the amount in the first food product, more preferably the amount is at least 20%, 50%, 100% or 200% higher than in the first food product.

In a yet further preferred embodiment, such second food product contains an amount of a specific plant miRNA which is at least 10% higher than the amount in the first food product, more preferably the amount is at least 20%, 50%, 100% or 200% higher than in the first food product.

Dietary supplements may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like.

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food e.g. enclosed in caps of food or beverage container for release immediately before consumption.

The dosage of miRNA for use according to the invention as food additive, of course, vary depending upon known factors, such as its mode and route of administration; the age, health and weight of the recipient; the nature and extent of the symptoms; the kind of concurrent treatment; the frequency of treatment; and the effect desired which can be determined by the expert in the field with normal trials, or with the usual considerations regarding the formulation of a miRNA.

The dosage of miRNA for use according to the invention in a pharmaceutical composition can be determined by the expert in the field with normal preclinical and clinical trials, or with the usual considerations regarding the formulation of pharmaceutical composition.

The pharmaceutical compositions may be administered as single dose or multiple doses.

The compositions according to the present invention may be in any galenic form that is suitable for administering to the animal body including the human body, more in particular in any form that is conventional for oral administration, e.g. in solid form, for example tablets, pills, granules, dragees, capsules, and effervescent formulations such as powders and tablets, or in liquid form, for instance in the form of solutions, emulsions or suspensions, for example as pastes and oily suspensions. The pastes may be filled into hard or soft shell capsules, whereby the capsules feature e.g. a matrix of (fish, swine, poultry, cow) gelatin, plant proteins or lignin sulfonate. Examples for other application forms are forms for transdermal, parenteral, topical or injectable administration. The pharmaceutical compositions may be in the form of controlled (delayed) release formulations.

In a preferred embodiment the compositions according to the invention are in the form of a tablet, a pill, a granule, a dragee, a capsule or an effervescent formulation.

In a yet further preferred embodiment, the present invention relates to a method of treating or preventing an inflammatory disease, comprising administering to a patient in need thereof a pharmaceutically effective amount of plant sRNA extract or plant miRNA.

In a yet further preferred embodiment, the present invention relates to a method of preventing an inflammatory disease, comprising administering to a human a plant sRNA extract or plant miRNA, which is preferably comprised in a dietary supplement, food or food additive. The human is in one preferred embodiment a patient in need thereof. In another embodiment the human is a healthy person, in particular a person not suffering from an inflammatory disease.

The dietary supplement may be administered as single dose or multiple doses.

In a yet further embodiment of the food product of the present invention or the method of method for producing a second food product, the miRNA is *F. vesca* miR168.

FIGURES LEGEND

FIG. 1: Examples of the sRNA profiles obtained according to Example 1. A. Ladder profile showing the six RNA markers in nucleotides (nt); B. Profile obtained by running a total RNA sample encompassing the high molecular weight fraction, identifiable by the 28S and 18S peaks, and the sRNA fraction of low molecular weight, on the left of the electropherogram. C-G. Examples of the sRNA fractions used in the experiments here presented. H. Electropherogram of a sample that has been excluded after analysis since high molecular weight RNA contamination (18S and 28S) is present.

FIG. 2: shows the sequences of duplex structures of *Fragaria vesca* FvmiR156 (A) FvmiR168 (B), *Oryza sativa* OsamiR168 (C) and a sGFP (D). me: methyl group.

Figure 3:
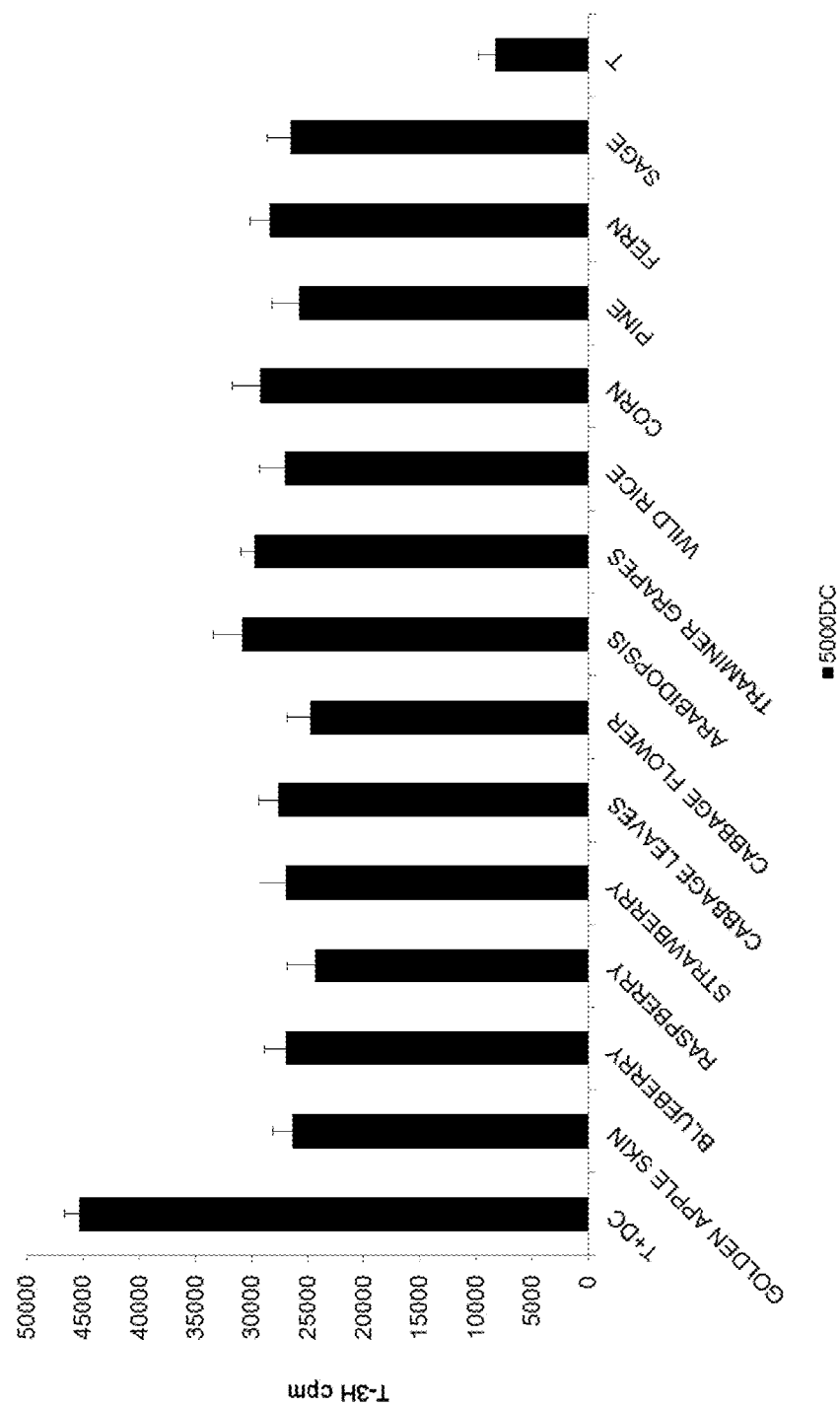

FIG. 3: Effects of different plant sRNA extracts on T cell proliferation. MLR results are shown. Any treatment is statistically significant with respect to the control (DC+ T w/o sRNA treatment)

Figure 4:
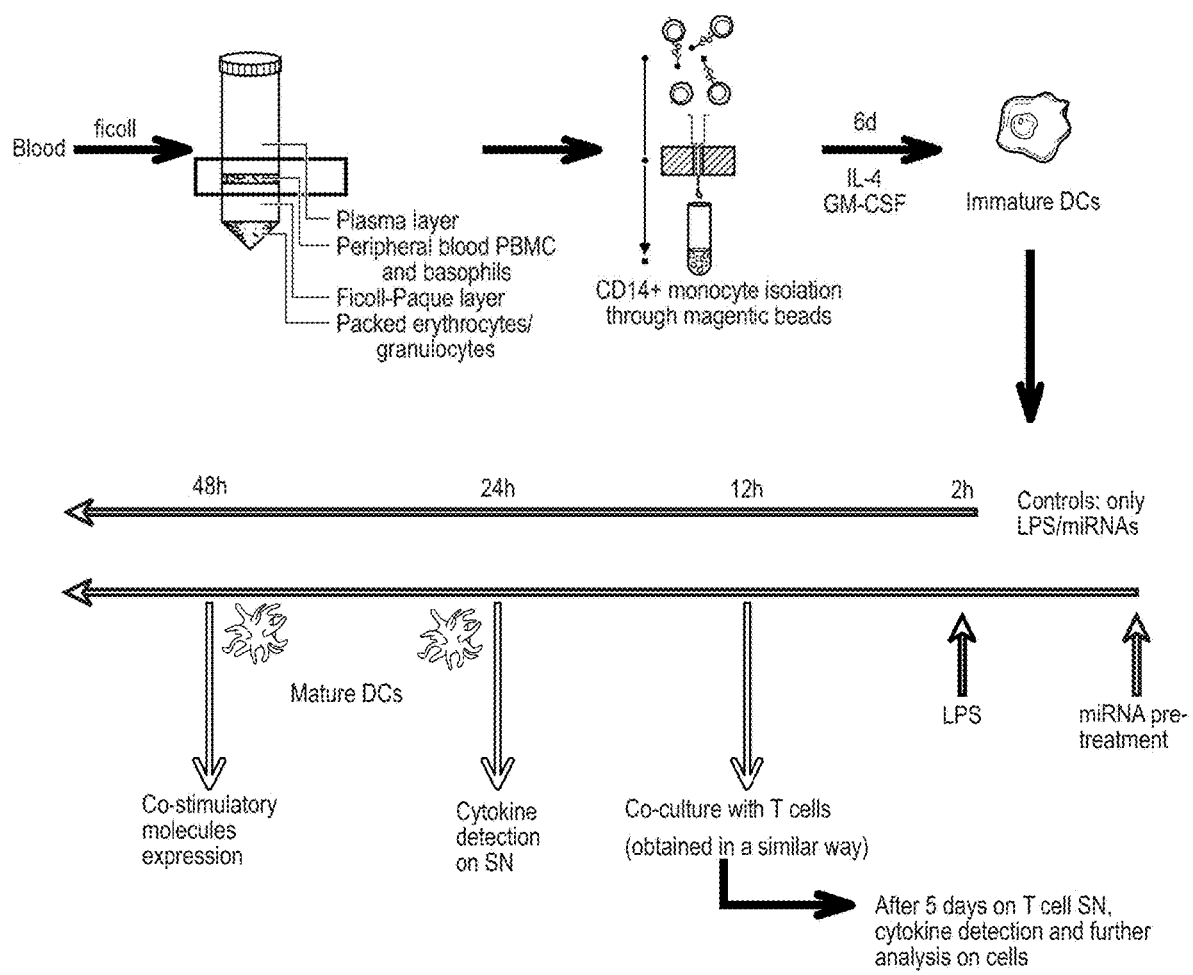

FIG. 4: shows the Experimental design to obtain dendritic cells for miRNA treatment and to evaluate the effect of plant miRNA on stimulated DC.

Figure 5:
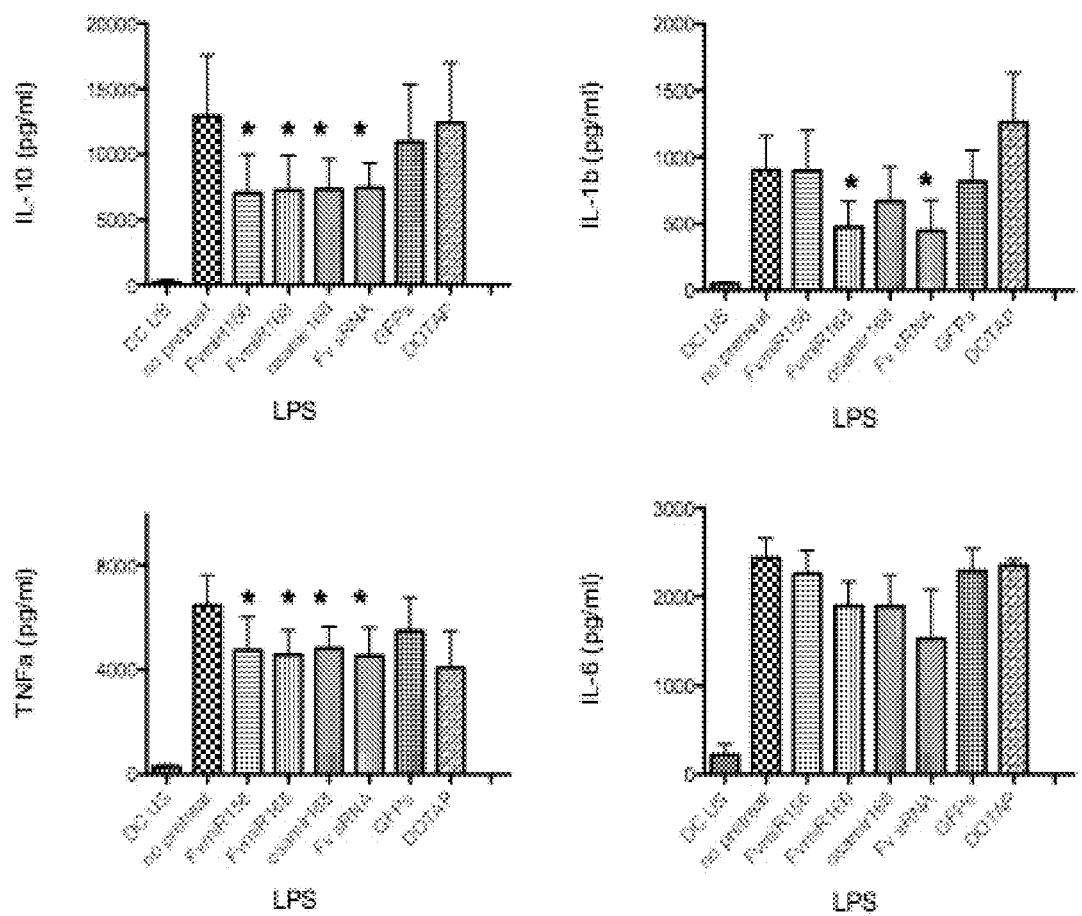
Figure 7:
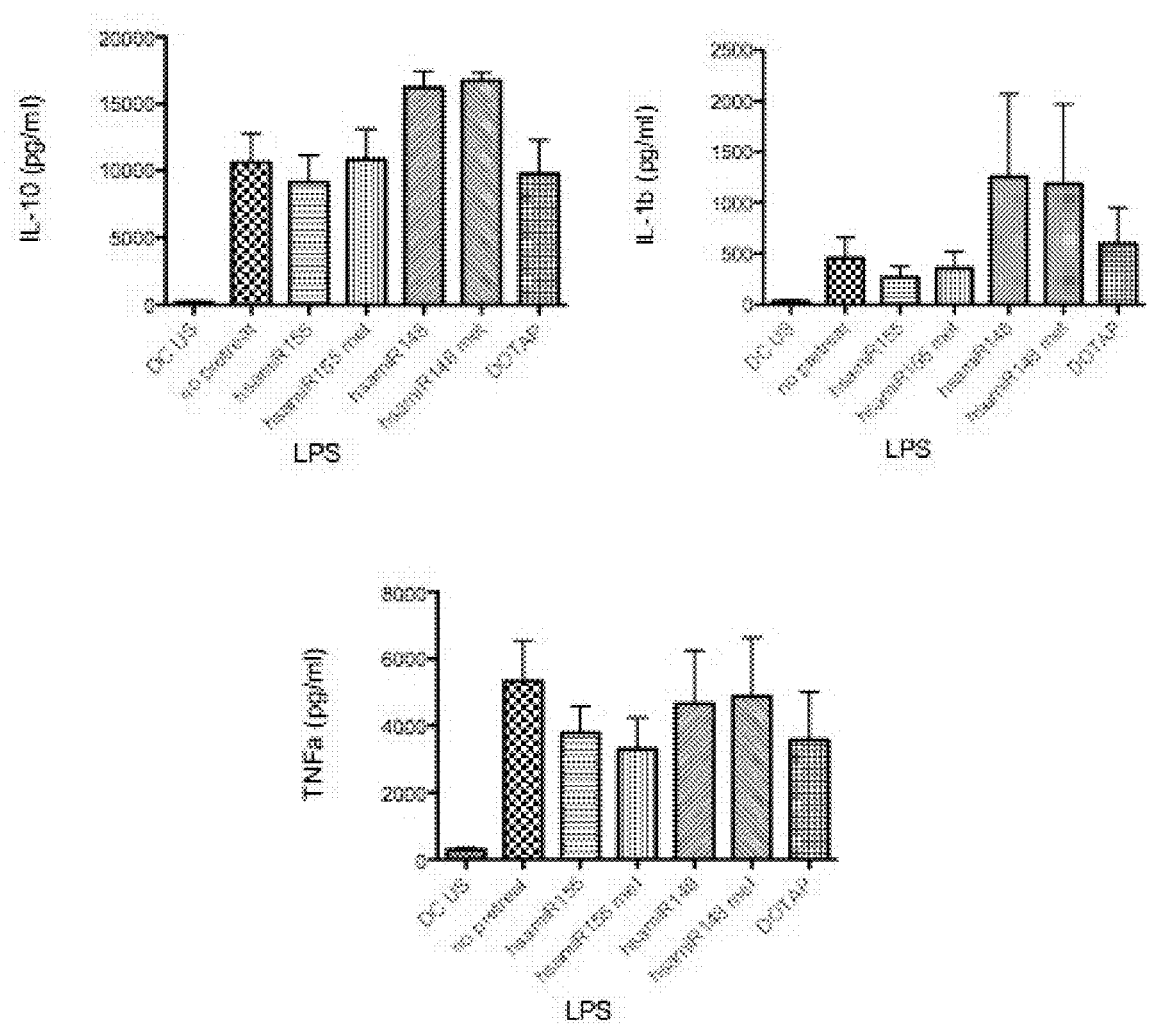
Figure 8:
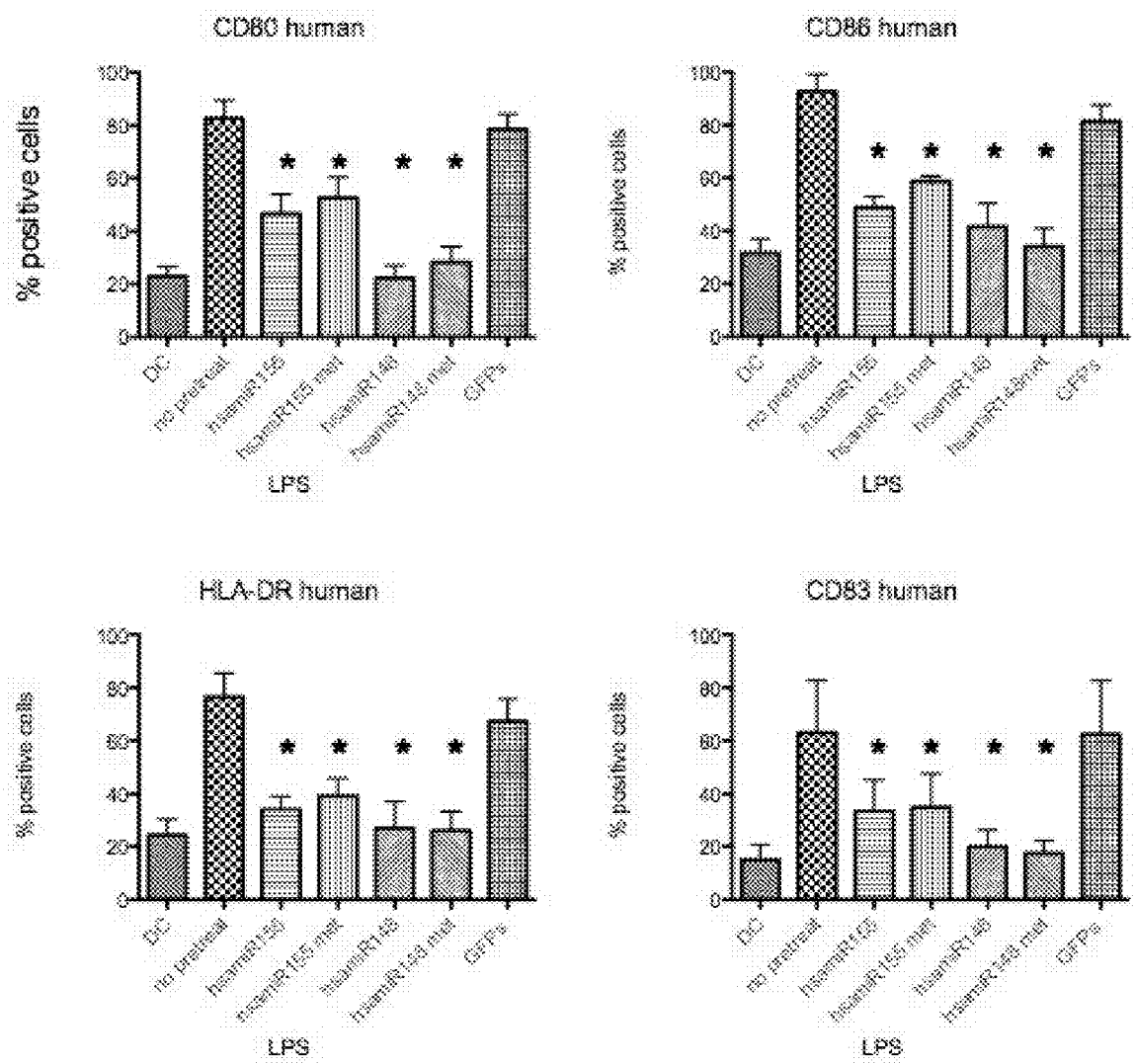

FIG. 5: Effects of plant miRNA treatment in DC immune function. Effects of miRNA treatment on IL-1$\beta$, TNF$\alpha$, IL-10 and IL-6 production. Mean+SD, N=5, *$p<0.05$, **$p<0.01$ T test, \$$p<0.05$, Kruskal Wallis test, treatment vs no pretreatment FIG. 6: Effects of plant miRNA treatment in DC immune function. Effects of miRNA treatment on costimulatory molecules expression. Mean+SD, N=3, *$p<0.05$, **$p<0.01$ T test, \$$p<0.05$, Kruskal Wallis test, treatment vs no pre-treatment FIG. 7: Effects of endogenous human miRNA treatment in DC immune function. Effects miRNA treatment on IL-1$\beta$, TNF$\alpha$, IL-10 production. Mean+SD, N=5, *$p<0.05$, **$p<0.01$ T test, \$$p<0.05$, Kruskal Wallis test, treatment vs no pretreatment FIG. 8: Effects of endogenous human miRNA treatment in DC immune function. Effects of miRNA treatment on costimulatory molecules expression. Mean+SD, N=5, *$p<0.05$, **$p<0.01$ T test, \$$p<0.05$, Kruskal Wallis test, treatment vs no pretreatment FIG. 9: Ability of T cells to produce INF$\gamma$ in response to LPS-loaded DCs previously exposed to different plant and human miRNAs as well as total FvsRNA fraction. Mean+SD, N=5, *$p<0.05$, **$p<0.01$ T test, § $p<0.05$, Kruskal Wallis test, treatment vs no pretreatment.

Figure 10:
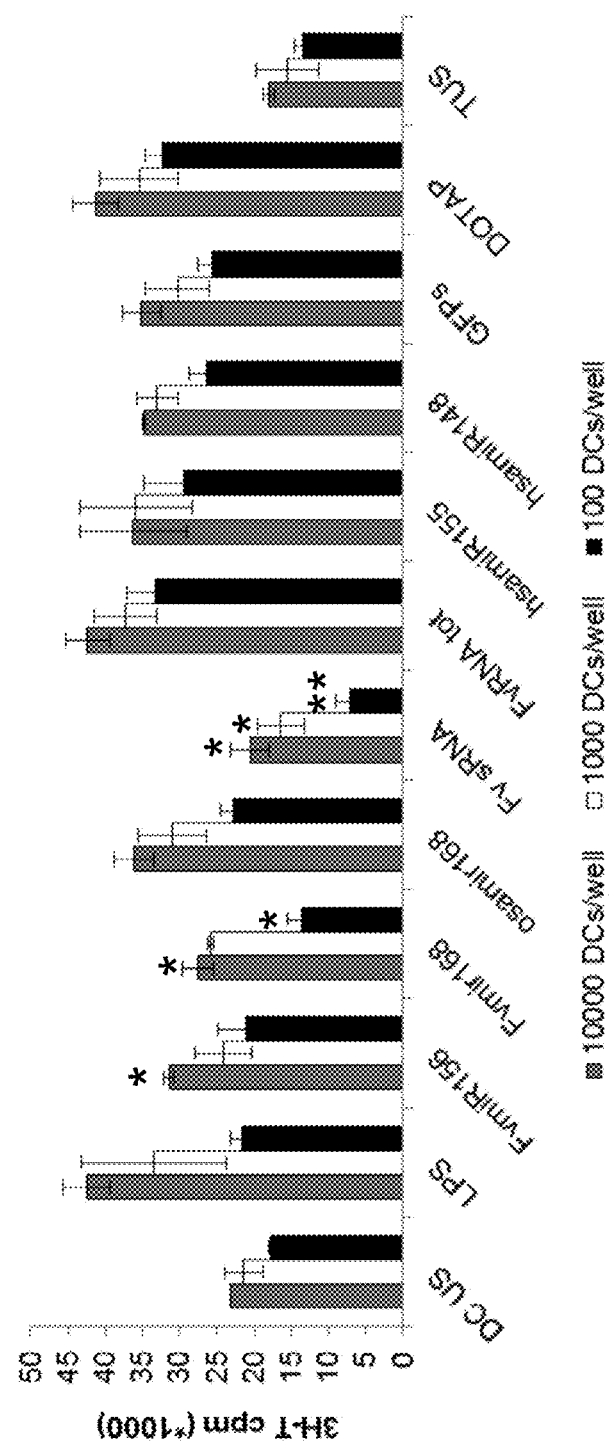

FIG. 10: Effects of miRNA treatment on T cell proliferation. MLR results after treatment with different plant and human miRNA as well as total FvRNA fraction are shown. Mean+SD, N=4, *$p<0.05$, **$p<0.01$ T test, treatment vs not pretreatment MLR assay showed that FvmiR168 and FvsRNA modulate T cell proliferation.

| Sequences |
|---|
| SEQ ID No. 1 corresponds to the sequence of methylated FvmiR156 (5'-UUGACAGAAGAGAGUGAGCACmeth-3'). |
| SEQ ID No. 2 corresponds to the sequence of methylated FvmiR156* (5'-AGCUCUUUCUCUUUCUGUCACUmeth-3'). |
| SEQ ID No. 3 corresponds to the sequence of methylated FvmiR168. (5'-UCGCUUGGUGCAGGUCGGGAAmeth-3') |
| SEQ ID No. 4 corresponds to the sequence of methylated FvmiR168* (5'-CCCGCCUUGCAUCAACUGAAUmeth-3'). |
| SEQ ID No. 5 corresponds to the sequence of methylated osamiR168. (5'-UCGCUUGGUGCAGAUCGGGACmeth-3'). |
| SEQ ID No. 6 corresponds to the sequence of methylated osamiR168* (5'-GAUCCCGCCUUGCACCAAGUGAAUmeth-3'). |
| SEQ ID No. 7 corresponds to the sequence of small duplex sGFP. (5'-AGAACGGCAUCAAAGCCAACU-3' (sGFP)). |
| SEQ ID No. 8 corresponds to the sequence of the second strand of small duplex sGFP (3'-UUGGCUUUGAUGCCGUUCUUUU-5' (asGFP)). |

EXAMPLES

Example 1

Preparation of a Plant sRNA Extracts and Synthesis of miRNAs miR156, miR168, osamiR168 and Small Duplex sGFP (FIGS. 1 and 2)

Plant sRNAs were extracted using the mirPremier microRNA Isolation Kit (Sigma-Aldrich) according to the manufacturer's protocol. We collected several plant materials, encompassing the plant kingdom: strawberry fruits from *Fragaria vesca* (cv. Hawaii 4), blueberry, raspberry fruits, apple skin, cabbage leaves and flowers; Traminer grape; fern leaves; *Arabidopsis thaliana* leaves; wild rice and corn. All of them were pulverized in liquid nitrogen. One hundred milligrams were mixed with the buffer provided in the kit. The small RNA fraction was separated from the high molecular weight RNA by the use of columns included in the kit. Small RNA was finally eluted using RNAse-free water.

After each extraction, samples will be analyzed using the Agilent RNA 6000 Nano Kit through the BioAnalyzer instrument. Examples of the sRNA profiles used in the patent are showed in FIG. 1. FIG. 1A shows the six RNA markers in nucleotides (nt); FIG. 1B shows the profile obtained by running a total RNA samples encompassing the high molecular weight fraction, identifiable by the 28S and 18S peaks, and the sRNA fraction of low molecular weight, on the left of the electropherogram. FIG. 1C-1G panels show examples of the sRNA fractions used in the experiments here presented. FIG. 1H shows a sample that has been excluded after the analysis since high molecular weight RNA contamination (18S and 28S) is present. Furthermore we analyzed each sRNA preparation using the Agilent Small RNA kit. Through BioAnalyzer analysis we characterized the size of the sRNA present in each fraction we use in the next experiments. Size determination has been assessed on the basis of the retention time with respect to the known sizes and timing of the ladder peaks. The fraction of interest is between 10 and 120 nucleotides (nt) for all the plant sRNA extracts. Synthetic plant small RNA duplexes (FIG. 2) were synthesized by Sigma Genosys and purified by HPLC. The annealing of small RNA strands and the methylation at 3' was performed as described by Sigma oligo synthesis service (http://www.sigmaaldrich.com/life-science/custom-oligos/sira-oligos.html). Upon arrival the small RNA duplexes were resuspended in RNAse-free water to the appropriate concentration.

Example 2

Evaluation of sRNAs Effects on the T Cell Proliferation (FIG. 3)

In a Mixed Lymphocyte Reaction (MLR) assay, human CD4+ T cells were co-cultured with allogenic human monocyte-derived DCs in presence or not (positive control) of the different plant sRNA extracts. The MLR is a functional assay which measures the proliferative response of lymphocytes from one individual (the responder) to lymphocytes from another individual (the stimulator). In detail, peripheral blood mononucleated cells were collected by Ficoll gradient centrifugation from healthy donor buffy coat. CD14+ monocytes were then isolated by a positive magnetic selection and differentiate in immature DCs in medium containing IL-4 and GM-CSF. After 5 days, such monocyte-derived DCs were collected and used for the following challenges experiments. For MLR, DCs were co-cultured in the presence of CD4+ T cells with or without the presence of sRNA extracts. In each experiment (this or the following) sRNAs or miRNAs are complexed with DOTAP, a liposomal transfection agent, which facilitates nucleic acid entry into the cells (Carvalho et al. TLR3 essentially promotes protective class I-restricted memory CD8+ T-cell responses to *Aspergillus fumigatus* in hematopoietic transplanted patients. Blood. 2012 Jan. 26; 119(4):967-77; Bourquin C et al. Immunostimulatory RNA oligonucleotides induce an effective anti-tumoral NK cell response through the TLR7. J Immunol. 2009 Nov. 15; 183(10):6078-86). DOTAP is also added to the control cells to exclude cross reactivity). Any sRNA extracts tested, used at the more physiological concentration retrieved in host biofluids (10 ng/ml) were able to attenuate the T cell proliferation (FIG. 3).

Example 3

Evaluation of miRNAs Effects on the Immune Cells Properties and their Ability to Respond to an Inflammatory Stimulus In in vitro experiments, human monocyte-derived DCs were exposed to the purified miRNAs (or *Fragaria vesca* pure sRNA extracts) and then pre-treated DCs were challenged with purified LPS, the lipopolysaccharide layer of bacterial wall. This experiment allowed determining the sRNA effect on the activation process and maturation of the DC through co-stimulatory molecules analysis by flow cytometry and detection of soluble factors such as cytokines by DC on culture medium. Co-stimulatory molecules expressions on DC cell surface are markers of proper activation and maturation of the immune cell. Increasing levels of these molecules promote DC-T cells contact and antigen presentation thus activating T cells and their survival, priming the proper adaptive immune response. Cytokines could enhance the cellular response (i.e pro-inflammatory cytokines as IL-6, TNFα, IL-11, IL-12p70, IL-23, INFγ, IL-17), promote type-2 response and thus favoring antibody production (IL-4, IL-13, IL-5) or down-regulate inflammatory process (IL-10, TGFβ).

In particular, comparing the levels of CD80, CD86, CD83 and the class II immuno-histocompatibility complex (MHCII o HLA-DR) of DC pre-exposed to miRNAs or treated with LPS alone evidence a possible attenuation effects of the specific miRNAs. In parallel by evaluating the released cytokine profiles the ability of DCs to properly respond to the stimuli was assessed. Measuring the level of pro-inflammatory (IL-6, TNFα, IL-1, IL-12p70) and anti-inflammatory (IL-10) cytokines, allowed appreciation of the immuno-modulatory ability of the specific miRNAs. For all treated DC, 24 h—IL-1β, TNFα, IL-10 production and 48 h—CD80, CD86, CD83 and MHCII expression were analyzed. The cells were then used in mixed lymphocyte reaction, where treated DCs were co-cultured in the presence of CD4+ T cells. INFγ production was evaluated on culture supernatants after 5 days.

The general experimental design is shown in FIG. 4.

Figure 6:
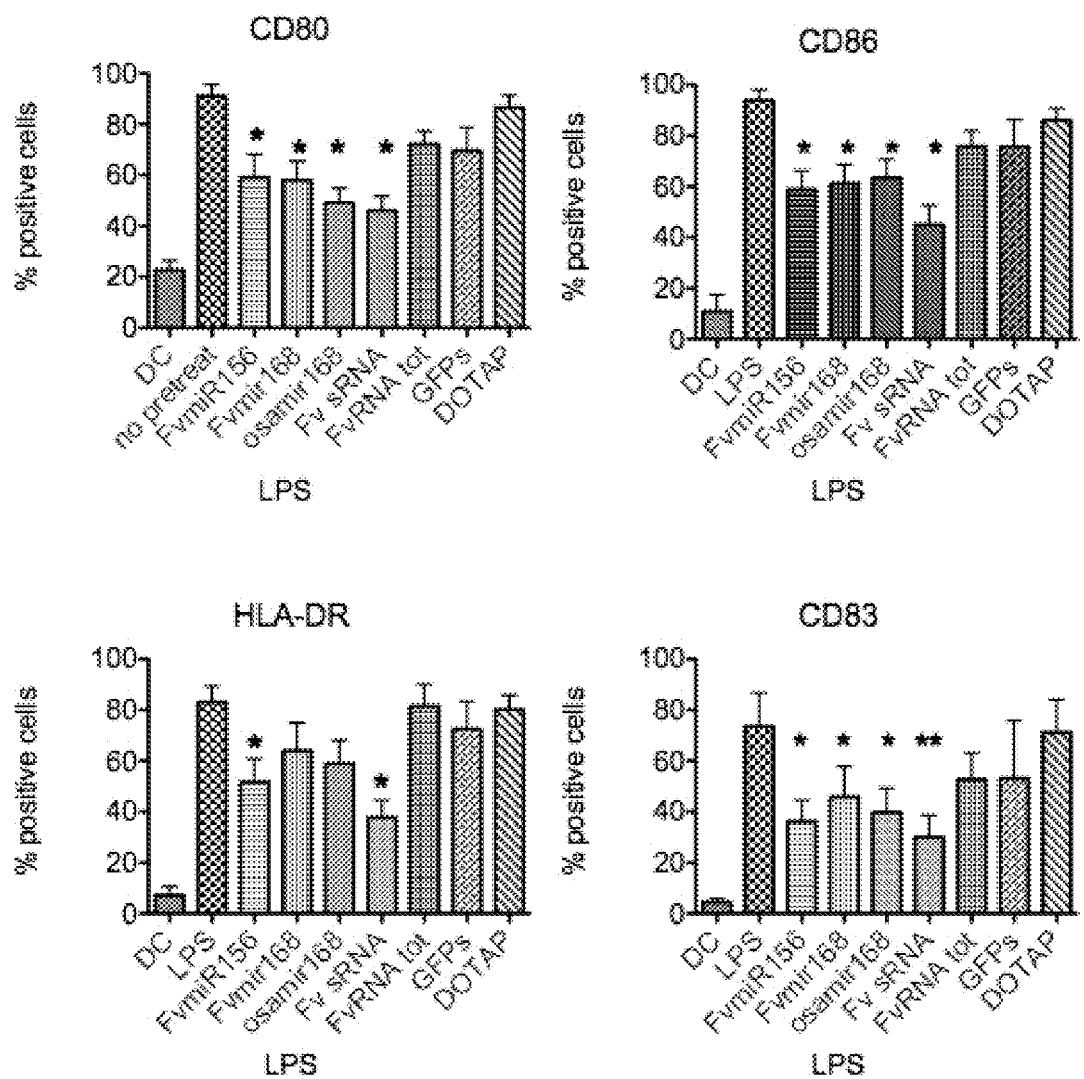

In a first set of experiments dendritic cells (DC) were treated with the following agents, respectively:
- *Fragaria vesca* specific small duplex miR156 (FvmiR156) (SEQ ID Nos. 1 and 2; FIG. 2A)
- *Fragaria vesca* small duplex miR168 (FvmiR168) (SEQ ID Nos. 3 and 4; FIG. 2B)
- rice small duplex osamiR168 (SEQ ID Nos. 5 and 6; FIG. 2C)
- *Fragaria vesca* total sRNAs fraction (FvsRNA)
- small duplex chemically modified green fluorescent protein sequence (sGFP; SEQ ID Nos. 7 and 8; FIG. 2D) (these already served as negative control for many groups (see Robbins M, 2008, Hum Gen Ther));
- *F. vesca* total high molecular weight RNA fraction (FvRNA)
- *E. coli* LPS (positive control)
- *E. coli* LPS after 2 h pre-exposure to the all nucleic acids above Several miRNAs concentrations were tested, ranging from the physiological (10 ng/ml) to the common experimental concentrations for nucleic acids (10 μg/ml, Liu Xl et al. (2010)). MicroRNA-148/152 impair innate response and antigen presentation of TLR-triggered dendritic cells by targeting CaMKIIα. J Immunol. 15; 185(12):7244-51; Carvalho et al. TLR3 essentially promotes protective class I-restricted memory CD8+ T-cell responses to *Aspergillus fumigatus* in hematopoietic transplanted patients. Blood. 2012 Jan. 26; 119(4):967-77; Bourquin C et al. Immunostimulatory RNA oligonucleotides induce an effective antitumoral NK cell response through the TLR7. J Immunol. 2009 Nov. 15; 183(10):6078-86). Even if the strongest inhibitory effects were seen at the highest concentrations, in order to avoid possible saturation effects of the system the Example showed results using the more physiological concentration of miRNAs retrieved in host biofluids (FIGS. 5 and 6). While the high molecular weight RNA fraction does not affect DCs activation by LPS, plant miRNAs and plant sRNA fraction modulate both cytokine and co-stimulatory expression.

In particular, plant sRNAs significantly attenuate IL-1β, TNFα and IL-10 production by LPS, as shown in FIG. 5. Moreover, FvmiR68 showed the strongest effects.

In addition, it could be shown that plant sRNAs limit the increase of CD80, CD86 and CD83 expression (FIG. 6).

In a further set of experiments (FIGS. 7 and 8), in order to investigate the possible effect of the presence of the methyl group in the plant miRNA sequence, which is not present in endogenous DC human miRNAs, two human miRNAs (miR148, miR155 and its star form miR155*), known to affect DC response to LPS (for a review, Zhan and Wu, Functional regulation of monocyte-derived dendritic cells by microRNAs. Protein Cell. 2012 July; 3(7):497-507) were used. DCs were treated with the following agents, respectively:
- human miR155
- human miR155 methylated
- human miR148
- human miR148 methylated The methylated miRNAs were synthesized by adding a methyl group at the 2'OH group of the 3' terminus.

The methyl group did not change the ability of human miRNAs to modulate the DC response to LPS.

Figure 9:
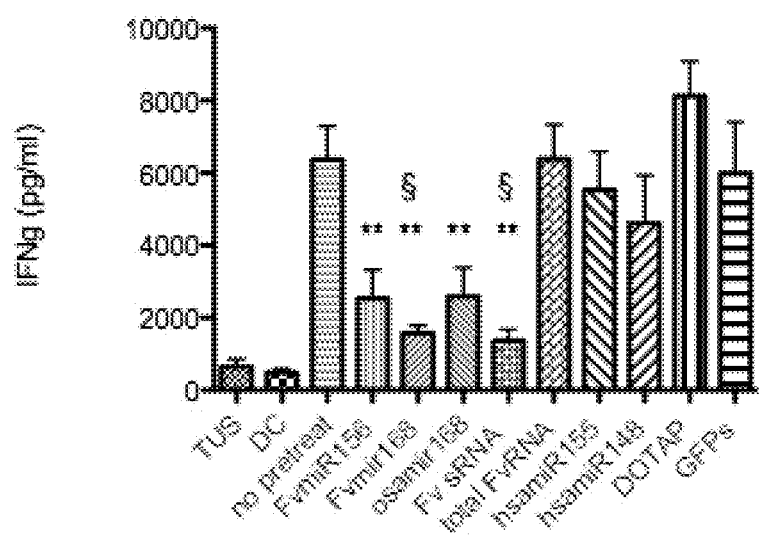

In further experiments to evaluate if not only sRNA fractions but also synthetic plant miRNA could modulate T cell proliferation, prior LPS treatment DCs were exposed for 2 h to:
- *Fragaria vesca* small duplex miR168 (FvmiR168) (SEQ ID Nos. 3 and 4; FIG. 2B)
- rice small duplex osamiR168 (SEQ ID Nos. 5 and 6; FIG. 2C)
- *Fragaria vesca* total sRNAs fraction (FvsRNA)
- hsamiR155
- hsamiR148 and then co-cultured with CD4+ T cells. sRNA- and miRNA-treated-DCs seem to have a lower immunostimulatory ability since LPS-induced IFN-γ is less produced by T cells (FIG. 9). MLR assay showed that FvmiR168 and FvsRNA modulate T cell proliferation (FIG. 10).

The invention claimed is:

1. A method for treating and/or preventing an inflammatory disease, comprising administering to a patient in need thereof a pharmaceutically effective amount of at least one micelle material, metal nanoparticle, nanoparticle, cationic lipid, cationic micelle, liposome or exosome comprising F. vesca miR168, wherein the inflammatory disease is characterized by an increase in expression or production of IL-1β, TNFα, or IL-10 or is characterized by an increase in CD4+ T cell proliferation, and wherein the F. vesca miR168 attenuates the CD4+ T cell proliferation or attenuates expression or production of IL-1β, TNFα, or IL-10.

2. A method for preventing an inflammatory disease, comprising administering to a human at least one micelle material, metal nanoparticle, nanoparticle, cationic lipid, cationic micelle, liposome or exosome comprising F. vesca miR168, wherein said human is a healthy human, or a human not suffering from said inflammatory disease, wherein the inflammatory disease is characterized by an increase in expression or production of IL-1β, TNFα, or IL-10 or is characterized by an increase in CD4+ T cell proliferation, and wherein the F. vesca miR168 attenuates the CD4+ T cell proliferation or attenuates expression or production of IL-1β, TNFα, or IL-10.

3. The method of claim 2, wherein said F. vesca miR168
   (a) is methylated at the 2'OH group at the 3' terminus, or
   (b) is synthetic miRNA, or
   (c) is purified from plant, or
   (d) is comprised in a plant sRNA extract.

4. The method of claim 2, wherein said F. vesca miR168 is comprised in a dietary supplement, food or food additive.

5. The method of claim 1, wherein said inflammatory disease is selected from the group consisting of chronic prostatitis, Glomerulonephritis, Hypersensitivities, Pelvic inflammatory disease, Reperfusion injury, Sarcoidosis, Vasculitis, Interstitial cystitis, normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's inflammatory disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

6. The method of claim 2, wherein said inflammatory disease is an autoimmune disease or an allergic disease.

7. The method of claim 6, wherein
   (a) said inflammatory disease is an autoimmune disease selected from the group consisting of multiple sclerosis, rheumatoid arthritis; psoriatic arthritis, discoid lupus erythematosus, systemic lupus erythematosus (SLE); ulcerative colitis; Crohn's disease; benign lymphocytic angiitis, autoimmune lymphoproliferative syndrome, sarcoidosis, autoimmune thrombocytopenic purpura, idiopathic thrombocytopenic purpura, pure red cell aplasia, Sjogren's syndrome, rheumatic disease, polymyalgia rheumatica, mixed connective tissue disease, inflammatory rheumatism, degenerative rheumatism, extra-articular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, ANCA-associated vasculitis, temporal arteritis, giant cell arteritis, Takayasu arteritis, Behcet's disease, antiphospholipid syndrome, myasthenia gravis, autoimmune haemolytic anaemia, Guillain-Barre syndrome, chronic immune polyneuropathy, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, Hashimoto's thyroiditis, fibromyalgia, chronic fatigue and immune dysfunction syndrome (CFIDS), primary myxedema, sympathetic ophthalmia, autoimmune inner ear disease, autoimmune uveitis, autoimmune chronic active hepatitis, collagen diseases, ankylosing spondylitis, periarthritis humeroscapularis, panarteritis nodosa, polyarteritis nodosa, chondrocalcinosis, Wegener's granulomatosis, microscopic polyangiitis, bullous skin disorders, pemphigoid, bullous pemphigoid, cicatricial pemphigoid, vitiligo, atopic eczema, eczema, chronic urticaria, autoimmune urticaria, normocomplementemic urticarial vasculitis, hypocomplementemic urticarial vasculitis, alopecia areata, alopecia universalis, alopecia totalis, Devic's disease, pernicious anemia, childhood autoimmune hemolytic anemia, idiopathic autoimmune hemolytic anemia, refractory or chronic Autoimmune Cytopenias, Prevention of development of Autoimmune Anti-Factor VIII Antibodies in Acquired Hemophilia A, Cold agglutinin disease, Neuromyelitis Optica, Stiff Person Syndrome, gingivitis, periodontitis, pancreatitis, myocarditis, gastritis, gout, gouty arthritis, idiopathic pericarditis, anti-synthetase syndrome, scleritis, macrophage activation syndrome, PAPA Syndrome, Blau's Syndrome, adult and juvenile Still's disease, cryopyrin associated periodic syndrome, Muckle-Wells syndrome, familial cold auto-inflammatory syndrome, neonatal onset multisystem inflammatory disease, chronic infantile neurologic cutaneous and articular syndrome, familial Mediterranean fever, Hyper IgD syndrome, Schnitzler's syndrome, autoimmune retinopathy, age-related macular degeneration, and TNF receptor-associated periodic syndrome (TRAPS), or (b) said inflammatory disease is an allergic disease selected from the group consisting of allergic respiratory disease, such as bronchial asthma, pediatric asthma, allergic asthma, atopic asthma, aspirin asthma, or allergic bronchitis, allergic nasal disease, such as allergic rhinitis, vernal catarrh, hay fever, or chronic allergic rhinitis, an allergic skin disease, such as atopic dermatitis, an allergic ocular disease, such as hay fever, seasonal allergic conjunctivitis, or chronic allergic conjunctivitis, hypersensitivity pneumonitis, contact dermatitis, and food allergy.

8. The method of claim 5, wherein said inflammatory disease is psoriasis.

9. The method of claim 2, wherein said inflammatory disease further comprises an increase in expression or production of at least one of inflammatory biomarker or wherein the inflammatory disease is characterized by a dysregulation of the cytokines or co-receptors in at least one cell or tissue of a patient.

10. The method of claim 1 or 2, wherein the cationic lipid is selected from DOTAP, DOPE, DC-Chol/DOPE, DOTMA, and DOTMA/DOPE.

* * * * *

SEQUENCE LISTING

```
<160> NUMBER OF SEQ ID NOS: 8

<210> SEQ ID NO 1
<211> LENGTH: 21
<212> TYPE: RNA
<213> ORGANISM: Artificial Sequence
<220> FEATURE:
<223> OTHER INFORMATION: methylated FvmiR156
<220> FEATURE:
<221> NAME/KEY: misc_feature
<222> LOCATION: (21)..(21)
<223> OTHER INFORMATION: cm

<400> SEQUENCE: 1
uugacagaag agagugagca n                                          21

<210> SEQ ID NO 2
<211> LENGTH: 22
<212> TYPE: RNA
<213> ORGANISM: Artificial Sequence
<220> FEATURE:
<223> OTHER INFORMATION: methylated FvmiR156*
<220> FEATURE:
<221> NAME/KEY: misc_feature
<222> LOCATION: (22)..(22)
<223> OTHER INFORMATION: um

<400> SEQUENCE: 2
agcucuuucu cuuucuguca cn                                         22

<210> SEQ ID NO 3
<211> LENGTH: 21
<212> TYPE: RNA
<213> ORGANISM: Artificial Sequence
<220> FEATURE:
<223> OTHER INFORMATION: methylated FvmiR168
<220> FEATURE:
<221> NAME/KEY: misc_feature
<222> LOCATION: (21)..(21)
<223> OTHER INFORMATION: 2'-O-methyladenosine

<400> SEQUENCE: 3
ucgcuuggug caggucggga n                                          21

<210> SEQ ID NO 4
<211> LENGTH: 21
<212> TYPE: RNA
<213> ORGANISM: Artificial Sequence
<220> FEATURE:
<223> OTHER INFORMATION: methylated FvmiR168*
<220> FEATURE:
<221> NAME/KEY: misc_feature
<222> LOCATION: (21)..(21)
<223> OTHER INFORMATION: um

<400> SEQUENCE: 4
cccgccuugc aucaacugaa n                                          21

<210> SEQ ID NO 5
<211> LENGTH: 21
<212> TYPE: RNA
<213> ORGANISM: Artificial Sequence
<220> FEATURE:
<223> OTHER INFORMATION: methylated osamiR168
<220> FEATURE:
<221> NAME/KEY: misc_feature
<222> LOCATION: (21)..(21)
<223> OTHER INFORMATION: cm

<400> SEQUENCE: 5
```

```
ucgcuuggug cagaucggga n                                                          21

<210> SEQ ID NO 6
<211> LENGTH: 24
<212> TYPE: RNA
<213> ORGANISM: Artificial Sequence
<220> FEATURE:
<223> OTHER INFORMATION: methylated osamiR168*
<220> FEATURE:
<221> NAME/KEY: misc_feature
<222> LOCATION: (24)..(24)
<223> OTHER INFORMATION: um

<400> SEQUENCE: 6
gaucccgccu ugcaccaagu gaan                                                       24

<210> SEQ ID NO 7
<211> LENGTH: 21
<212> TYPE: RNA
<213> ORGANISM: Artificial Sequence
<220> FEATURE:
<223> OTHER INFORMATION: small duplex sGFP

<400> SEQUENCE: 7
agaacggcau caaagccaac u                                                          21

<210> SEQ ID NO 8
<211> LENGTH: 21
<212> TYPE: RNA
<213> ORGANISM: Artificial Sequence
<220> FEATURE:
<223> OTHER INFORMATION: asGFP

<400> SEQUENCE: 8
uuggcuuuga ugccguucuu u                                                          21
```